(12) United States Patent
Toda

(10) Patent No.: US 11,266,428 B2
(45) Date of Patent: Mar. 8, 2022

(54) ULTRASONIC TRANSDUCER AND MANUFACTURING METHOD OF ULTRASONIC TRANSDUCER

(71) Applicant: OLYMPUS CORPORATION, Hachioji (JP)

(72) Inventor: Masaya Toda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 553 days.

(21) Appl. No.: 16/369,476

(22) Filed: Mar. 29, 2019

(65) Prior Publication Data

US 2019/0223900 A1 Jul. 25, 2019

Related U.S. Application Data

(63) Continuation of application No. PCT/JP2016/079114, filed on Sep. 30, 2016.

(51) Int. Cl.
| | |
|---|---|
| *H02N 2/00* | (2006.01) |
| *A61B 17/32* | (2006.01) |
| *H04R 17/00* | (2006.01) |
| *H04R 17/10* | (2006.01) |

(Continued)

(52) U.S. Cl.
CPC ........ *A61B 17/320068* (2013.01); *A61B 17/320092* (2013.01); *H04R 3/00* (2013.01); *H04R 17/00* (2013.01); *H04R 17/10* (2013.01); *H04R 31/00* (2013.01); *A61B 2017/320089* (2017.08)

(58) Field of Classification Search
None
See application file for complete search history.

(56) References Cited

U.S. PATENT DOCUMENTS

| | | | | |
|---|---|---|---|---|
| 5,800,448 | A * | 9/1998 | Banko ............ | A61B 17/320016 606/169 |
| 2003/0212392 | A1* | 11/2003 | Fenton .......... | A61B 17/320068 606/28 |

(Continued)

FOREIGN PATENT DOCUMENTS

| | | |
|---|---|---|
| JP | S60-109399 A | 6/1985 |
| JP | H07-303635 A | 11/1995 |
| JP | 2015-33090 A | 2/2015 |

OTHER PUBLICATIONS

Apr. 23, 2020 Office Action issued in Chinese Patent Application No. 201680089736.8.

(Continued)

*Primary Examiner* — Olisa Anwah
(74) *Attorney, Agent, or Firm* — Oliff PLC

(57) ABSTRACT

An ultrasonic transducer includes driving source attached to an outer periphery of a bolt with being sandwiched between a distal side block and a proximal side block in a direction along a longitudinal axis, and the driving source includes a piezoelectric element generating ultrasonic vibration by an electric energy being supplied. By transmission of the ultrasonic vibration generated in the piezoelectric element, the ultrasonic transducer in a state in which a first vibration node that is generated in the driving source and a second vibration node that is generated in the bolt are prevented from being displaced with respect to each other in the direction along the longitudinal axis.

20 Claims, 10 Drawing Sheets

(51) Int. Cl.
   *H04R 31/00* (2006.01)
   *H04R 3/00* (2006.01)

(56) References Cited

U.S. PATENT DOCUMENTS

| | | | |
|---|---|---|---|
| 2005/0187514 A1* | 8/2005 | Rabiner | A61B 18/1492 604/22 |
| 2007/0060926 A1* | 3/2007 | Escaf | A61F 9/00745 606/107 |
| 2008/0214967 A1* | 9/2008 | Aranyi | A61B 17/320068 601/3 |
| 2009/0216157 A1* | 8/2009 | Yamada | A61B 17/320092 601/2 |
| 2009/0270854 A1* | 10/2009 | Yachi | A61B 17/320092 606/27 |
| 2009/0275864 A1 | 11/2009 | Hirai | |
| 2009/0318944 A1* | 12/2009 | Kimura | A61B 17/320068 606/169 |
| 2009/0318945 A1* | 12/2009 | Yoshimine | A61B 17/320068 606/169 |
| 2010/0167235 A1* | 7/2010 | Vercellotti | A61C 1/07 433/86 |
| 2010/0331872 A1* | 12/2010 | Houser | A61N 7/02 606/169 |
| 2017/0274420 A1* | 9/2017 | Toda | B06B 1/0611 |

OTHER PUBLICATIONS

Dec. 6, 2016 International Search Report issued in International Patent Application No. PCT/JP2016/079114.
Apr. 2, 2019 International Preliminary Report on Patentability issued in International Application No. PCT/JP2016/079114.
Aug. 8, 2017 Office Action issued in Japanese Application No. 2017-521254.

* cited by examiner

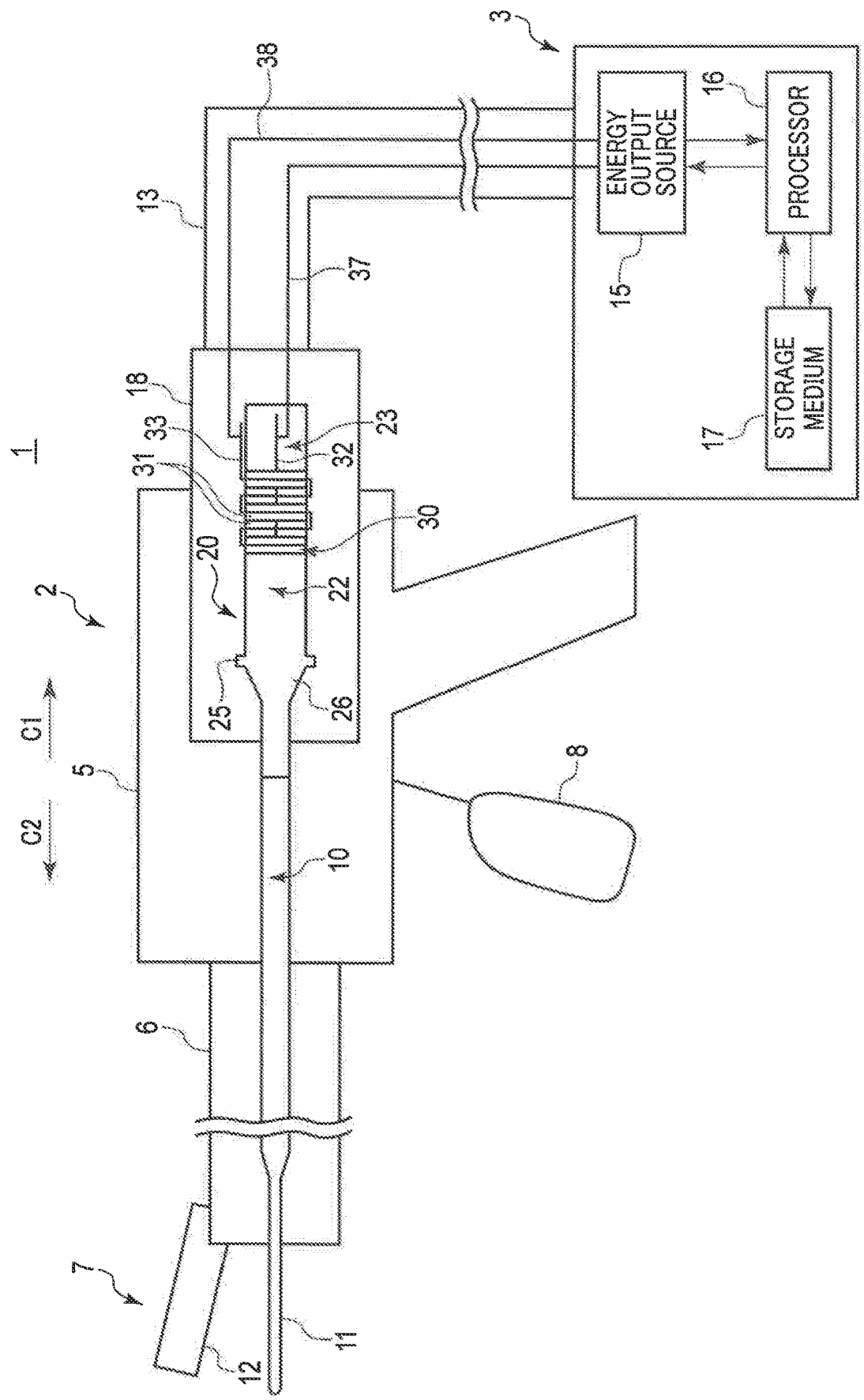
F I G. 1

ULTRASONIC TRANSDUCER AND MANUFACTURING METHOD OF ULTRASONIC TRANSDUCER

CROSS-REFERENCE TO RELATED APPLICATIONS

This is a Continuation Application of PCT Application No. PCT/JP2016/079114, filed Sep. 30, 2016, the entire contents of which are incorporated herein by reference.

BACKGROUND OF THE INVENTION

1. Field of the Invention

The present invention relates to an ultrasonic transducer including a piezoelectric element which is configured to generate ultrasonic vibration by an electric energy being supplied, and a method of manufacturing the ultrasonic transducer.

2. Description of the Related Art

U.S. Patent Application Publication No. 2009/275864 A1 discloses an ultrasonic treatment instrument that treats a treatment target using ultrasonic vibration. This ultrasonic treatment instrument is provided with an ultrasonic transducer including a piezoelectric element which is configured to generate ultrasonic vibration by an electric energy being supplied. In this ultrasonic transducer, a distal portion of a bolt is connected to a distal side block so that the bolt anti the distal side block are integrally formed. A driving unit including a piezoelectric element is attached to an outer periphery of the bolt. A proximal portion of the bolt is connected to a proximal side block so that the proximal side block is fastened to the outer periphery of the bolt. The driving unit is sandwiched between the distal side block and the proximal side block, and a pressing force toward the distal side acts on the driving unit from the proximal side block.

BRIEF SUMMARY OF THE INVENTION

According to one aspect of the invention, an ultrasonic transducer including: a bolt which includes a proximal end and a distal end, and which is extended along a longitudinal axis from the proximal end to the distal end; a distal side block to which a distal portion of the bolt is connected; a proximal side block to which a proximal portion of the bolt is connected; and a driving source which includes a piezoelectric element, and which is attached to an outer periphery of the bolt in a state in which the driving source is sandwiched between the distal side block and the proximal side block in a direction along the longitudinal axis, the piezoelectric element being configured to generate ultrasonic vibration by an electric energy being supplied, by transmission of the ultrasonic vibration generated in the piezoelectric element, and the driving source being configured to vibrate together with the bolt, the distal side block, and the proximal side block in a state in which a first vibration node that is generated in the driving source and a second vibration node that is generated in the bolt are prevented from being displaced with respect to each other in the direction along the longitudinal axis.

According to one another aspect of the invention, a manufacturing method of an ultrasonic transducer, the method including: attaching a driving source which includes a piezoelectric element, to an outer periphery of a bolt which is extended along a longitudinal axis from a proximal end to a distal end; sandwiching the driving source between a distal side block, to which a distal portion of the bolt is connected, and a proximal side block, to which a proximal portion of the bolt is connected, in a direction along the longitudinal axis; generating ultrasonic vibration by an electric energy being supplied to the piezoelectric element, and vibrating the driving source together with the bolt, the distal side block, and the proximal side block by the generated ultrasonic vibration; in a state in which the bolt, the distal side block, the proximal side block, and the driving unit vibrate together, detecting a relative position in the direction along the longitudinal axis between a first vibration node that is generated in the driving unit and a second vibration node that is generated in the bolt; and on a basis of a detection result of the relative position between the first vibration node and the second vibration node, adjusting a vibration state in an outer vibration system that generates the first vibration node and a vibration state in an inner vibration system that generates the second vibration node in a manner such that the first vibration node and the second vibration node are prevented from being displaced with respect to each other in the direction along the longitudinal axis.

Advantages of the invention will be set forth in the description which follows, and in part will be obvious from the description, or may be learned by practice of the invention. The advantages of the invention may be realized and obtained means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view illustrating a treatment system using an ultrasonic transducer according to a first embodiment.

DETAILED DESCRIPTION OF THE INVENTION

First Embodiment

Figure 2:
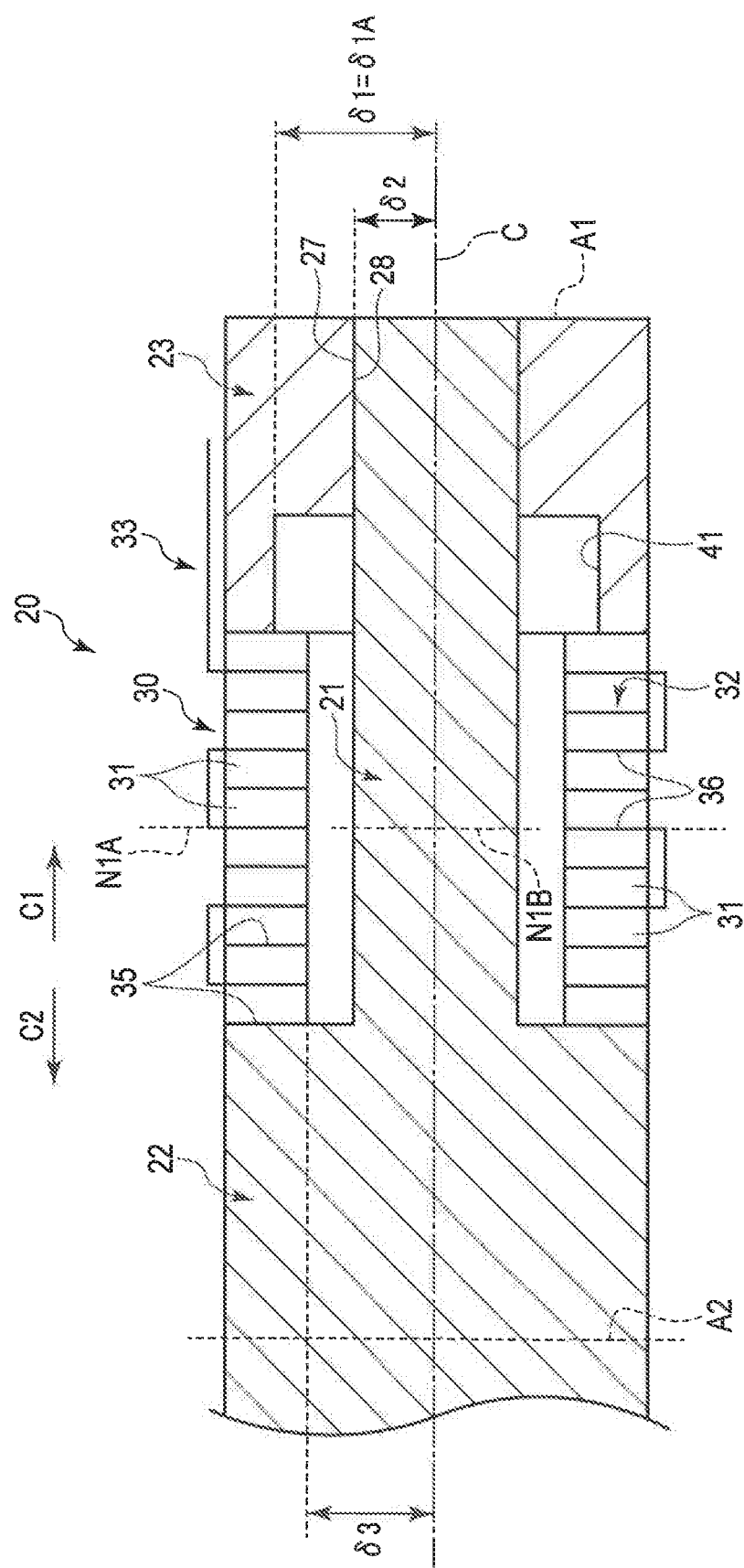
FIG. 2 is a cross-sectional view schematically illustrating a configuration of the ultrasonic transducer according to the first embodiment.

A first embodiment of the present invention will be described with reference to FIGS. 1 to 4. FIG. 1 is a view illustrating a treatment system 1 using an ultrasonic transducer 20 according to the present embodiment. As shown in FIG. 1, the treatment system 1 includes an ultrasonic treatment instrument 2 and an energy control device 3. The ultrasonic treatment instrument 2 includes a holdable housing 5, and a shaft 6 that is attached to the housing 5. The shaft 6 is extended substantially straight. Here, in the ultrasonic treatment instrument 2, a side on which the housing 5 is positioned with respect to the shaft 6 is a proximal side (arrow C1 side), and an opposite side to the proximal side is a distal side (arrow C2 side). Therefore, the shaft 6 is attached to the housing 5 from the distal side. Furthermore, in the ultrasonic treatment instrument 2, an end effector 7 is provided in a part on the distal side with respect to the shaft 6.

A handle 8 is rotatably attached to the housing 5. By the handle 8 rotating relative to the housing 5, the handle 8 opens or closes relative to the housing 5. Furthermore, a rod member (probe) 10 is inserted through the shaft 6. The rod member 10 is made of a material with high vibration transmission property, such as a titanium alloy. The rod member 10 is extended from the inside of the housing 5 through the inside of the shaft 6 toward the distal side. The rod member 10 includes a rod protrusion 11 that protrudes from the distal end of the shaft 6 toward the distal side. A jaw 12 is rotatably attached to the distal end portion of the shaft 6. The jaw 12 and the handle 8 are interconnected via a movable member (not shown) that is extended through the inside of the shaft 6. By the handle 8 opening or closing with respect to the housing 5, the movable member moves to the proximal side or the distal side. This causes the jaw 12 to rotate with respect to the shaft 6, thereby opening or closing a space between the jaw 12 and the rod protrusion 11. In the present embodiment, the end effector 7 is composed of the rod protrusion 11 and the jaw 12. A treatment target such as biological tissue is gripped, between jaw 12 and the rod protrusion 11, thereby being treated.

In one embodiment, a rotary knob (not shown) as a rotary operation member is attached to the housing 5, and the rotary knob is rotatable with respect to the housing around the central axis of the shaft 6. In this case, by rotating the rotary knob the shaft 6, the end effector 7, and the rod member 10 rotate together with respect to the housing 5 around the central axis of the shaft 6. Also, in one embodiment, the jaw 12 is not provided so that the end effector 7 is composed of the rod protrusion 11 only. In this case, neither the handle 8 nor the movable member described above is provided. In this case, the rod protrusion 11 has a hook shape, a spatula shape, or a blade shape, etc.

The ultrasonic transducer 20 is connected to the rod member 10 from the proximal side inside the housing 5. In the present embodiment, the ultrasonic transducer 20 is housed in the transducer case 18 and is supported by the transducer case 18. By attaching the transducer case 18 to the housing 5 from the proximal side, the ultrasonic transducer 20 is connected to the rod member 10. In the present embodiment, the distal end of the ultrasonic transducer 20 is directly connected to the proximal end of the rod member 10. Furthermore, in the present embodiment, one end of a cable 13 is connected to the transducer case 18. The other end of the cable 13 is detachably connected to the energy control device 3.

In one embodiment, the transducer case 18 is not provided. In this case, the ultrasonic transducer 20 is supported by the housing 5, and one end of the cable 13 is connected to the housing 5. In another embodiment, the ultrasonic transducer 20 is indirectly connected to the rod member 10 via one or more relay members (not shown). In this case, the relay member is made of a material with high vibration transmission property, such as a titanium alloy. In the embodiment in which the aforementioned rotary knob is provided, by rotating the rotary knob, the ultrasonic transducer 20 rotates together with the shaft 6, the end effector 7, and the rod member 10, with respect to the housing 5 around the central axis of the shaft 6.

FIG. 2 is a view illustrating the configuration of the ultrasonic transducer 20. As shown in FIG. 2, the ultrasonic transducer 20 includes a bolt (shaft) 21 having a longitudinal axis C as a central axis. Here, one side in the direction along the longitudinal axis C coincides with the proximal side (arrow C1 side), and the other side in the direction along the longitudinal axis C coincides with the distal side (arrow C2 side). The bolt 21 is extended substantially straight along the longitudinal axis C from the proximal end to the distal end.

As shown in FIGS. 1 and 2, in the ultrasonic transducer 20, the distal portion of the bolt 21 is connected to a distal side block (front mass) 22 an the present embodiment, the distal side block 22 is integral with the bolt 21. The distal side block 22 and the bolt 21 are made of, for example, a titanium alloy, an aluminum alloy, SUS, etc. The distal side block 22 may be made of the same material as that of the bolt 21 or may be made of a different material from that of the bolt 21. Furthermore, the distal side block 22 forms the distal end of the ultrasonic transducer 20 and is connected to the rod member 10 or the relay member. In the present embodiment, the distal side block 22 is provided with a supported portion 25 such as a flange that is supported by the transducer case 18 or the housing 5, and a horn 26 whose cross sectional area substantially perpendicular to the longitudinal axis C decreases toward the distal side. In the embodiment in which the relay member is provided between the ultrasonic transducer 20 and the rod member 10, the supported portion 25 and the horn 26 described above may be provided in the relay member.

In the ultrasonic transducer 20, the proximal portion of the bolt 21 is connected to the proximal side block (back mass) 23. In the present embodiment, a proximal side block 23 is formed in a ring shape that covers the outer periphery of the bolt 21. The outer periphery of the proximal portion of the bolt 21 is provided with a male screw portion 27 as a first engagement. The inner periphery of the proximal side block 23 is provided with a male screw portion 28 as a second engagement that is engaged with the first engagement. In the present embodiment, the male screw portion 27 is extended from the proximal end the bolt 21 toward the distal side, and the female screw portion 28 is extended from the proximal end of the proximal side block 23 toward the distal side. By engaging the female screw portion 28 with the male screw portion 27, that is, by screwing them together, the proximal side block 23 is fastened to the outer periphery of the bolt 21. Therefore, in the present embodiment, the proximal side block 23 is a fastening member that is fastened to the outer periphery of the bolt 21.

The proximal sine block 23 is made of, for example, a titanium alloy, an aluminum alloy, SUS, etc. Here, the proximal side block 23 may be made of the a same material as that of the distal side block 22 or may be made of a different material from that of the distal side block 22. Furthermore, in the present embodiment, the proximal end of the proximal side block 23 is substantially aligned with the proximal end of the bolt 21 in the direction along the longitudinal axis C, so that the proximal end of the ultrasonic transducer 20 is composed of the proximal end of the proximal side block 23 and the proximal end of the bolt 21.

A driving unit (driving source) 30 is attached to the outer periphery of the bolt 21. The driving unit 30 is sandwiched between the distal side block 22 and the proximal side block 23 in a direction along the longitudinal axis C. Then, the driving unit 30 is pressed toward the distal side by the proximal side block 23. The driving unit (actuator) 30 includes ten piezoelectric elements 31 in the present embodiment. The piezoelectric elements 31 are made of a material such as ceramics etc. that is different in material property (physical property) such as a rigidity modulus from a material for the bolt 21. The piezoelectric elements 31 convert electric energy into vibration energy. Each of the piezoelectric elements 31 is formed in a ring shape, and the bolt 21 is inserted through each of the piezoelectric elements 31. A minimum of one piezoelectric element 31 is required.

The driving unit 30 includes electrode members 32 and 33 made of a conductive material such as metal. The electrode member 32 includes six electrode ring portions 35 in the present embodiment, and the electrode member 33 includes five electrode ring portions 36 in the present embodiment. The bolt 21 is inserted through each of the electrode ring portions 35 and the electrode ring portions 36. Each of the piezoelectric elements 31 is sandwiched between a corresponding one of the electrode ring portions 35 and a corresponding one of the electrode ring portions 36 in the direction along the longitudinal axis C. One end of the electric wiring 37 is connected to the electrode member 32. One end of the electric wiring 38 is connected to the electrode member 33. The number of electrode ring portions 35 and 36 is determined according to the number of piezoelectric elements 31. In any case, each of the piezoelectric elements 31 is sandwiched between a corresponding one of the electrode ring portions 35 and a corresponding one of the electrode ring portions 36. The ultrasonic transducer 20 is formed as described above. Thus, in the present embodiment, the ultrasonic transducer 20 is a bolt-clamped Langevin-type transducer.

The energy control device 3 includes an energy output source 15, a processor 16, and a storage medium 17. The electric wires 37 and 38 are extended through the inside of cable 13, and the other ends of electric wires 37 and 38 are connected to the energy output source 15. The energy output source 15 includes a conversion circuit, etc., that converts an electric power supplied from, e.g., an electric power supply such as a battery or an outlet, into an electric energy that is to be supplied to the driving unit 30 of the ultrasonic transducer 20. The energy output source 15 outputs this converted electric energy. The electric energy output from the energy output source 15 is supplied to the driving unit 30 via the electric wires 37 and 38. The energy output source 15 outputs an AC power to the driving unit 30 at any frequency within a predetermined frequency range, for example.

The processor 16 as a controller is composed of an integrated circuit including a CPU (Central Processing Unit), an ASIC (Application Specific Integrated Circuit), an FPGA (Field Programmable Gate Array), etc. Processing in the processor 16 is performed according to programs stored in the processor 16 or the storage medium 17. The storage medium 17 stores processing programs for use in the processor 16 as well as parameters, tables, etc., for use in processing in the processor 16. The processor 16 controls an output of an electric energy from the energy output source 15 to the driving unit 30. In the present embodiment, the processor 16 detects an output current and an output voltage related to an electric energy from the energy output source 15 to the driving unit 30, thereby detecting a phase difference $\Delta\theta$ between the output current and the output voltage. Thereafter, the processor 16 adjusts a frequency f in the output from the energy output source 15 within a predetermined frequency range $\Delta f$ in a manner such that the phase difference $\Delta\theta$ becomes zero. That is, the processor 16 performs PLL (Phase Lock Loop) control in which the frequency f in an output of an electric energy is adjusted in a manner such that the phase difference $\Delta\theta$ becomes zero.

By an electric energy being supplied from the energy output source 15 to the driving unit 30, a voltage is applied between the electrode members 32 and 33, so that a voltage is applied to each of the piezoelectric elements 31. This causes each of the piezoelectric elements 31 to convert an electric energy into a vibration energy, so that ultrasonic vibration is generated in the piezoelectric elements 31. The generated ultrasonic vibration is transmitted to the rod member 10 and is then transmitted from the proximal side toward the distal side through the rod member 10 up to the rod protrusion 11. The end effector 7 treats a treatment target such as biological tissue, etc., using the ultrasonic vibration transmitted to the rod protrusion 11. In a state in which ultrasonic vibration is transmitted in the ultrasonic transducer 20 and the rod member 10, a vibrating body including the ultrasonic transducer 20 and the rod member 10 vibrates at any frequency within a predetermined frequency range. Therefore, in the ultrasonic transducer 20, the bolt 21, the distal side block 22, the proximal side block 23, and the driving unit 30 vibrate together by ultrasonic vibration generated in the piezoelectric element 31. At this time, the vibrating body longitudinally vibrates while a vibration direction is substantially parallel to the longitudinal axis C. A predetermined frequency range is 46 kHz or more and 48 kHz or less in one example, and is 46.5 kHz or more and 47.5 kHz or less in another example.

In a state in which the vibrating body vibrates at any frequency within a predetermined frequency range, one of vibration anti-nodes is generated in a distal end of the vibrating body, that is, the distal end of the rod member 10. Then, a vibration anti-node A1 as one of the vibration anti-nodes is generated in a proximal end of the vibrating body, that is, the proximal end of the ultrasonic transducer 20. Among vibration anti-nodes, the vibration anti-node A1 is positioned most proximally. In the present embodiment, a vibration anti-node A2, which is separated from the vibration anti-node A1 by a half of a wavelength toward the distal side, is generated in the distal side block 22. In the present embodiment, in a state in which the vibrating body vibrates at any frequency within a predetermined frequency range, a first vibration node N1A is generated in the driving unit 30 while a second vibration node N1B is generated in the bolt 21. Each of the vibration nodes N1A and N1B is a vibration node between the vibration anti-node A1 and the vibration anti-node A2 and is positioned away by a quarter of a wavelength from the vibration anti-node A1 toward the distal side.

In one embodiment, insulating rings (not shown) made of an electrically-insulating material are provided between the driving unit 30 and the distal side block 22, and between the driving unit 30 and the proximal side block 23, respectively. Furthermore, an insulating tube (not shown) made of an electrically-insulating material is provided between the inner periphery of the driving unit 30 and the outer periphery of the bolt 21. Accordingly, an electric energy supplied to the driving unit 30 is prevented from being supplied to the distal side block 22, the proximal side block 23, and the bolt 21. In addition, in one embodiment, an electric energy different from the electric energy supplied to the driving unit 30 is output from the energy output source 15. For example, an electric energy different from the electric energy supplied to the driving unit 30 is supplied to each of the rod protrusion 11 and the jaw 12. As a result, a high-frequency current flows through a treatment target gripped between the jaw 12 and the rod protrusion 11.

As shown in FIG. 2, the inner periphery of the proximal side block 23 is provided with a non-contact portion 41 that is spaced apart from the outer periphery of the bolt 21. In the present embodiment, the non-contact portion 41 is extended from the distal end of the proximal side block 23 toward the proximal side so that the non-contact portion 41 is adjacent to the distal side of the female screw portion 28 as the second engagement. Here, the female screw portion 28 is in contact with the outer periphery of the bolt 21 at the male screw portion 27. Therefore, the inner diameter of the proximal side block 23 at the non-contact portion 41 is larger than the inner diameter of the proximal side block 23 at the female screw portion 28, and a distance $\delta1$ in a radial direction from the longitudinal axis C to the non-contact portion 41 is larger than a distance $\delta2$ in the radial direction from the longitudinal axis C to the female screw portion 28. In one embodiment, the inner diameter of the proximal side block 23 at the non-contact portion 41 is larger than the inner diameter of the driving unit 30, and the distance $\delta1$ in the radial direction from the longitudinal axis C to the non-contact portion 41 corresponds to a distance $\delta1A$ which is larger than a distance $\delta3$ in the radial direction from the longitudinal axis C to the inner periphery of the driving unit 30. The distance $\delta3$ in the radial direction from the longitudinal axis C to the inner periphery of the driving unit 30 is larger than the distance 32 in the radial direction from the longitudinal axis C to the female screw portion 28.

Next, a manufacturing method, function, and effects of the ultrasonic transducer 20 according to the present embodiment will be described. In manufacturing the ultrasonic transducer 20, first, the driving unit 30 including the piezoelectric elements 31 is attached to the outer periphery of the bolt 21. Then, the female screw portion (second engagement) 28 of the proximal side block 23 is screwed to the male screw portion (first engagement) 27 of the bolt 21 so that the proximal side block 23 is fastened to the outer periphery of the bolt 21. Accordingly, the driving unit 30 is sandwiched between the distal side block 22 and the proximal side block 23, so that a predetermined pressing force acts on the driving unit 30 from the proximal side block 23.

When the ultrasonic transducer 20 is assembled as described above, an electric energy is supplied from the energy output source 15 to the driving unit 30, so that the ultrasonic transducer 20 is vibrated by ultrasonic vibration. At this time, the PLL control described above is performed by the processor 16. Then, in a state in which the ultrasonic transducer 20 is vibrating, a relative position between the first vibration node N1A and the second vibration node N1B described above is detected. In the present embodiment, an output current and an output voltage related to an electric energy supplied to the driving unit 30 are detected, and a relative position between the vibration nodes N1A and N1B is detected on the basis of the phase difference $\Delta\theta$ between the output current and the output voltage. In one embodiment, a relative position between the vibration nodes N1A and N1B is detected on the basis of the frequency f in an output from the energy output source 15 in addition to the phase difference $\Delta\theta$.

Here, the bolt 21 is different from each piezoelectric element 31 in terms of material property (physical property) such as a rigidity modulus. In addition, each member constituting the ultrasonic transducer 20 is different in shape, etc. In a state in which the ultrasonic transducer 20 vibrating by ultrasonic vibration generated in the piezoelectric element 31, vibration in an outer vibration system that generates the first vibration node N1A and the vibration in an inner vibration system that generates the second vibration node N1B are affected by material properties such as a rigidity modulus, etc., as well as shapes, of constituent members of the ultrasonic transducer 20, such as the bolt 21, the distal side block 22, the proximal side block 23, the piezoelectric elements 31, etc. That is, a rigidity of each part of the ultrasonic transducer 20 on the basis of a physical property, the shape, etc., of each constituent member of the ultrasonic transducer 20 affects each of vibration of the outer vibration system and vibration of the inner vibration system. Therefore, a difference in a material property, the shape, etc., between constituent members of the ultrasonic transducer 20 may cause the first vibration node N1A generated in the driving unit 30 and the second vibration node N1B generated in the bolt 21 to be displaced with respect to each other in the direction along the longitudinal axis C. For example, in a case where the piezoelectric elements 31 are made of a material having a higher rigidity modulus than that of a material for the bolt 21, the second vibration node N1B may be positioned on the distal side with respect to the first vibration node N1A. On the other hand, for example, in a case where the piezoelectric elements 31 are made of a material having a lower rigidity modulus than that of a material for the bolt 21, the second vibration node N1B may be positioned on the proximal side with respect to the first vibration node N1A. In the present embodiment, the outer vibration system is composed of the driving unit 30 and the proximal side block 23, while the inner vibration system is composed of the bolt 21.

Figure 3A:
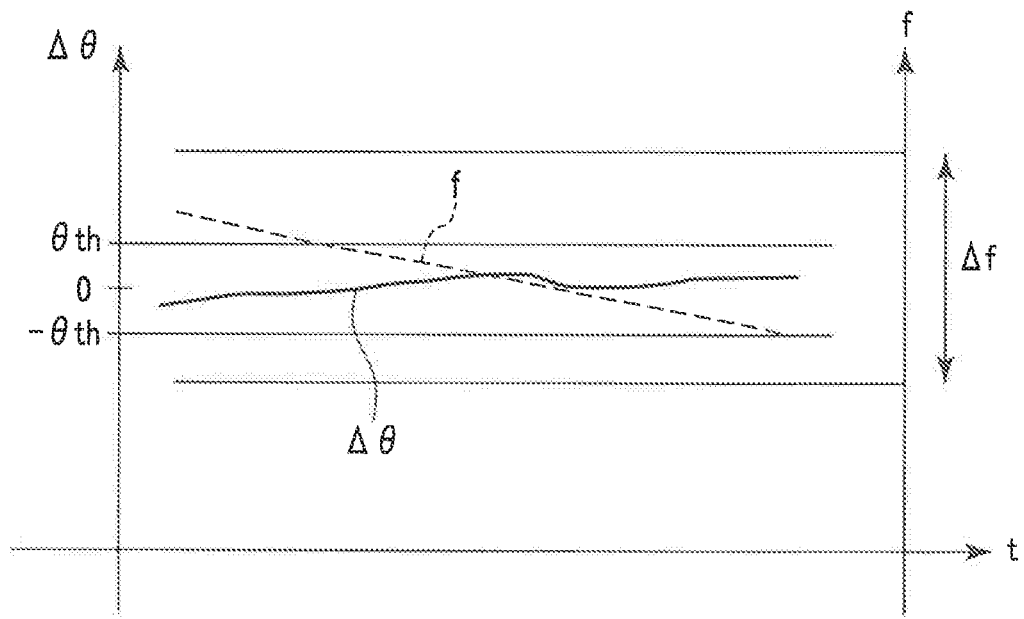
FIG. 3A is a schematic view illustrating an example of a change with time of a phase difference between an output current and an output voltage to a driving unit and an example of a change with time of a frequency in an output from start of PLL control, in a state in which a first vibration node and a second vibration node are not displaced with respect to each other.
Figure 3B:
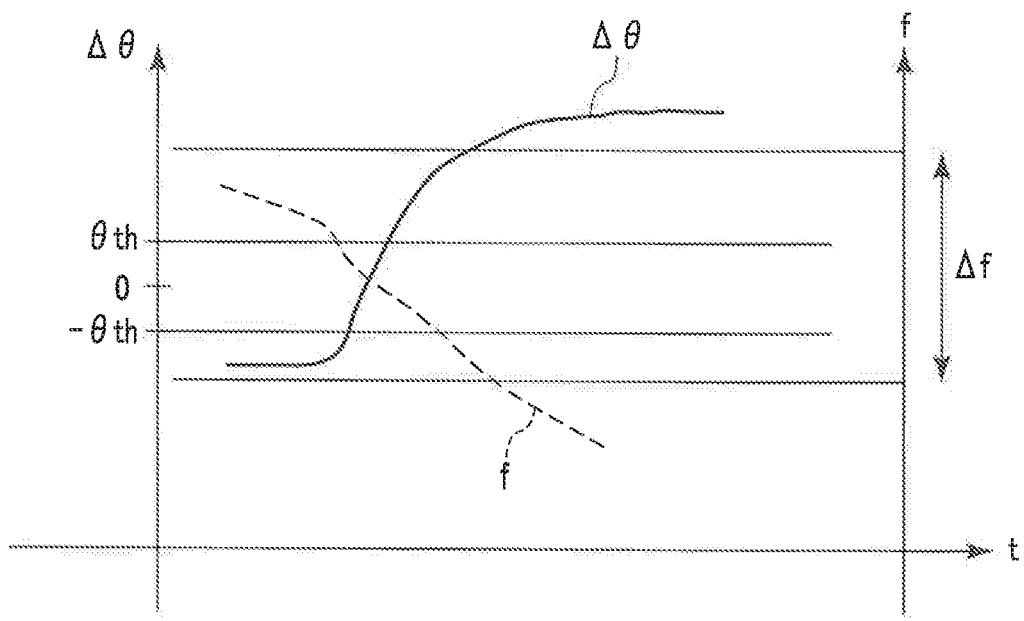
FIG. 3B is a schematic view illustrating an example of a change with time of a phase difference between an output current and an output voltage to the driving unit and an example of a change with time of a frequency in an output changes from start of the PLL control, in a state in which the second vibration node is positioned on a distal side with respect to the first vibration node.

Each of FIGS. 3A and 3B is a view illustrating an example of a change with time of the phase difference $\Delta\theta$ between an output current and an output voltage to the driving unit 30 and an example of a change with time of the frequency f in an output, after start of the PLL control. FIG. 3A shows a state in which the first vibration node N1A and the second vibration node N1B are not displaced with respect to each other. FIG. 3B shows a state in which the second vibration node N1B is positioned on the distal side with respect to the first vibration node N1A. In each of FIGS. 3A and 3B, the abscissa axis represents an elapsed time t while the ordinate axes represent the phase difference $\Delta\theta$ and the frequency f. In each of FIGS. 3A and 3B, a change over time in the phase difference $\Delta\theta$ is indicated by a solid line while a change over time in the frequency f is indicated by a broken line.

As shown in FIG. 3A, in the case where the vibration nodes N1A and N1B are not displaced with respect to each other in the direction along the longitudinal axis C, the phase difference $\Delta\theta$ changes at zero or in the vicinity of zero by the PLL control. Therefore, an absolute value of the phase difference $\Delta\theta$ is maintained smaller than a predetermined threshold $\theta$th over time. Furthermore, when the ultrasonic transducer 20 continues to vibrate, heat is generated by vibration. As heat is generated, the frequency f gradually decreases over time by the PLL control. At this time, the frequency f decreases within the predetermined frequency range $\Delta f$ over time.

In the case shown in FIG. 3B in which the second vibration node N1B is positioned on the distal side with respect to the first vibration node N1A, immediately after start of the PLL control, vibration of the driving unit 30 including the piezoelectric elements 31, that is, vibration of the outer vibration system has a great effect, whereas vibration of the bolt 21, that is, vibration of the inner vibration system has a small effect. Therefore, an output current is delayed with respect to an output voltage, so that the phase difference $\Delta\theta$ becomes negative. In this case also, the frequency f decreases over time by the PLL control. When heat is generated by vibration and the frequency f decreases to a certain extent, the effect of vibration of the bolt (shaft) 21 increases. When the effect of the vibration system of the inner vibration system including the bolt 21 increases, an output current advances with respect to an output voltage, so that the phase difference $\Delta\theta$ is inverted to positive. Furthermore, when the effect of vibration of the bolt 21 increases, vibration of the driving unit 30 as a control target of the PLL control by the processor 16 is controlled on the basis of vibration of the bolt 21 (inner vibration system) that is different in vibration state from the vibrating unit 30 (outer vibration system). That is, the PLL control is not properly performed. Therefore, after the phase difference $\Delta\theta$ is inverted to positive, the phase difference $\Delta\theta$ does not change to negative. When a certain period of time passes, an absolute value of the phase difference $\Delta\theta$ becomes larger than the predetermined threshold $\theta$th, for example, larger than 10°. Furthermore, when the effect of vibration of the inner vibration system increases, the decrease rate of the frequency f increases, and the frequency f sharply decreases over time. In addition, since the PLL control is not properly performed, in some cases, the frequency f may decrease beyond the predetermined frequency range $\Delta f$.

In the case where the second vibration node N1B is positioned on the proximal side with respect to the first vibration node N1A, when the PLL control is started, the phase difference $\Delta\theta$ is inverted from positive to negative, for example. After the phase difference $\Delta\theta$ is inverted to negative, an absolute value of the phase difference $\Delta\theta$ becomes larger than the predetermined threshold $\theta$th without the phase difference $\Delta\theta$ changing to positive. In the case where the second vibration node N1B is positioned on the proximal side with respect to the first vibration node N1A, the frequency f within the predetermined frequency range $\Delta f$ may instantaneously change beyond the predetermined frequency range $\Delta f$.

Since the phase difference $\Delta\theta$ and the frequency indicate a changing tendency such as described above, in the present embodiment, the relative position between the vibration nodes N1A and N1B can be detected on the basis of the phase difference $\Delta\theta$ and the frequency f. For example, in one embodiment, it is determined that the vibration nodes N1A and N1B are shifted with respect to each other on the basis that the phase difference $\Delta\theta$ is inverted between positive and negative after the electric energy is started to be supplied to the piezoelectric elements 31, and that after the phase difference $\Delta\theta$ is inverted between positive and negative, an absolute value of the phase difference $\Delta\theta$ becomes larger than the predetermined threshold $\theta$th without the phase difference $\Delta\theta$ changing between positive and negative. Furthermore, since the phase difference $\Delta\theta$ and the frequency f indicate a changing tendency such as described above, in the present embodiment, it is possible to detect on the basis of the phase difference $\Delta\theta$ and the frequency f, whether the second vibration node N1B is displaced toward the distal side with respect to the first vibration node N1A, or is displaced toward the proximal side with respect to the first vibration node N1A.

In the present embodiment, when the relative position between the vibration nodes N1A and N1B is detected, on the basis of the detection result, the inner diameter of the proximal side block 23 at the non-contact portion 41 is adjusted, and the distance $\delta 1$ in the radial direction from the longitudinal axis C to the non-contact portion 41 is adjusted. The change in distance $\delta 1$ causes a change in cross sectional area perpendicular to the longitudinal axis C of the proximal side block 23 within the range in which the non-contact portion 41 is extended, so that the shape of the proximal side block 23 changes. The change in shape of the proximal side block 23 causes a change in rigidity (mass) of the proximal side block 23, thereby changing the vibration state in the outer vibration system including the driving unit and the vibration state in the inner vibration system including the bolt 21. Therefore, the distance $\delta 1$ affects the vibration in the outer vibration system and the vibration in the inner vibration system, so that the vibration state is adjusted in each of the outer vibration system and the inner vibration system by adjusting the distance $\delta 1$.

In addition, when the vibration state in each of the outer vibration system and the inner vibration system changes, the relative position between the vibration nodes N1A and N1B changes. Therefore, by the proximal side block 23 being adjusted in shape rigidity by adjusting the distance $\delta 1$, the relative position between the vibration nodes N1A and N1B is adjusted. In the present embodiment, the distance $\delta 1$ is adjusted so as to adjust the shape and rigidity of the proximal side block 23 in a manner such that the first vibration node N1A generated in the driving unit 30 and the second vibration node N1B generated in the bolt 21 are prevented from being displaced with respect to each other in the direction along the longitudinal axis C. Accordingly, the vibration state in each of the outer vibration system and the inner vibration system is adjusted in a manner such that the mutual displacement of the vibration nodes N1A and N1B is prevented.

Figure 4:
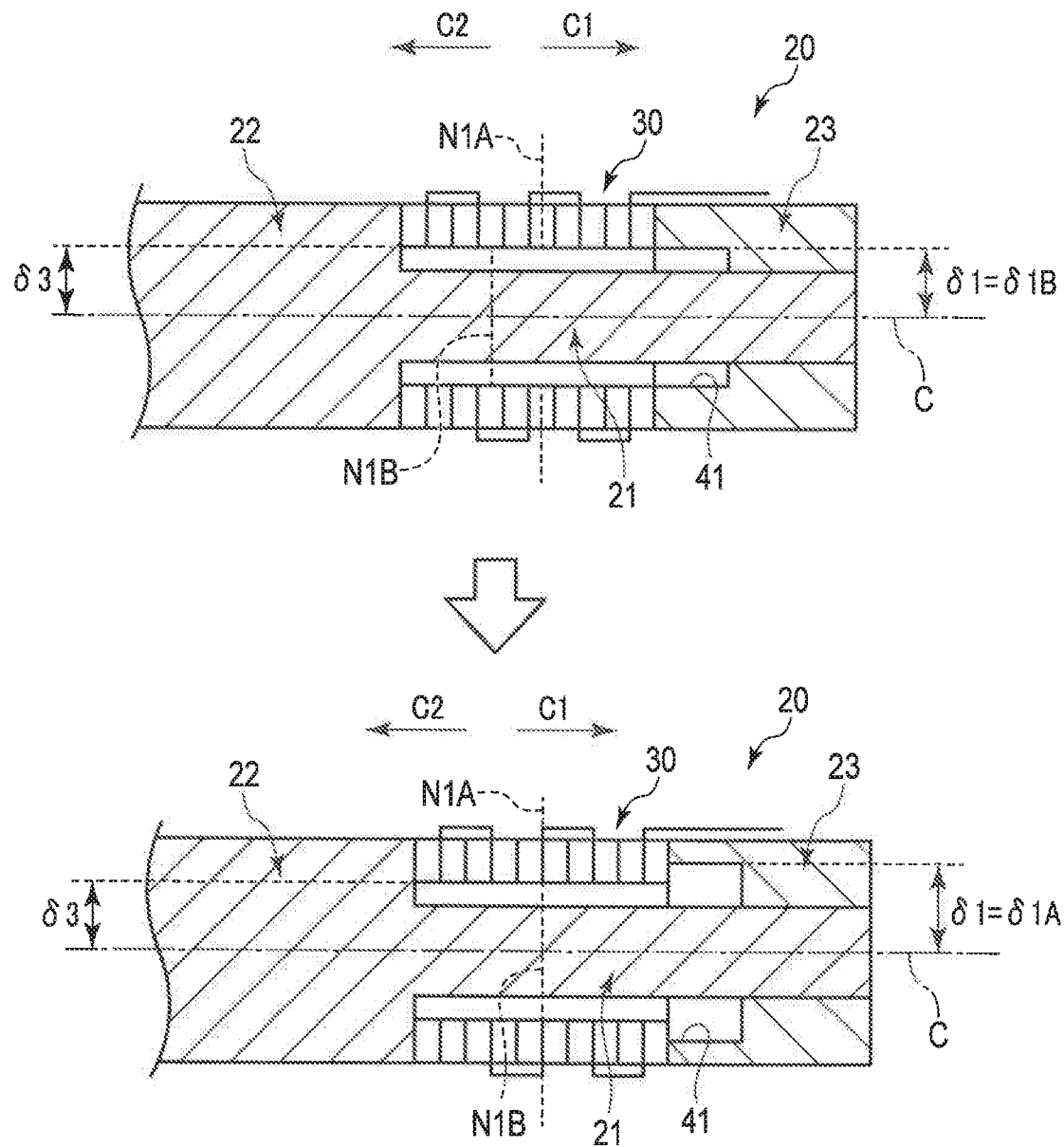
FIG. 4 is a schematic view illustrating an example of a method in which a mutual displacement of the first vibration node and the second vibration node is prevented by adjusting a distance in a radial direction from a longitudinal axis to a non-contact portion in the first embodiment.

FIG. 4 is a view for illustrating an example of a method in which the mutual displacement of the first vibration node N1A and the second vibration node N1B is prevented by adjusting the distance δ1 in the radial direction from the longitudinal axis C to the non-contact portion 41. In the example shown in FIG. 4, in the ultrasonic transducer 20 before the distance δ1 is adjusted, the distance δ1 in the radial direction from the longitudinal axis C to the non-contact portion 41 corresponds to a distance δ1B which is substantially equal to the distance δ3 in the radial direction from the longitudinal axis C to the inner periphery of the driving unit 30. In addition, the second vibration node N1B is positioned on the distal side with respect to the first vibration node N1A. In the example shown in FIG. 4, the distance δ1 is increased from the distance δ1B to the distance δ1A on the basis of the detection result of the relative position between the vibration nodes N1A and N1B. This changes the shape of the proximal side block 23, thereby changing the rigidity, the mass, etc., of the proximal side block 23. In the example shown in FIG. 4, the distance δ1 is increased without changing any material property such as a rigidity modulus of the proximal side block 23. Therefore, by the adjustment of the distance δ1, the rigidity of the proximal side block 23 reduces and the mass of the proximal side block 23 decreases. By the proximal side block 23 changing in shape, the vibration state in each of the outer vibration system and the inner vibration system changes, so that the relative position between the vibration nodes N1A and N1B changes. In the ultrasonic transducer 20 having the distance δ1 being adjusted to the distance δ1A, the mutual displacement of the vibration nodes N1A and N1B is prevented.

In the present embodiment, as described above, the shape of the proximal side block 23 is adjusted by adjusting the distance δ1 when the ultrasonic transducer 20 is manufactured, so that the mutual displacement of the vibration nodes N1A and N1B prevented. The vibration nodes N1A and N1B are prevented from being shifted with respect to each other due to the shape of the proximal side block 23 including the distance δ1. Accordingly, in a state in which the ultrasonic transducer 20 is vibrating by ultrasonic vibration at the time of, for example, using the ultrasonic treatment instrument 2, the PLL control is properly performed by the processor 15, so that the phase difference Δθ between an output current and an output voltage to the driving unit 30 is maintained at zero or in the vicinity of zero. In addition, by preventing the mutual displacement between the vibration nodes N1A and N1B, irregular vibration. (e.g., lateral vibration, torsional vibration, etc.) other than the longitudinal vibration is also prevented from occurring. This reduces not only a loss in the conversion of an electric energy into a vibration energy by the ultrasonic transducer 20, but also heat generation due to the energy loss in the ultrasonic transducer 20.

(Modifications)

Figure 5:
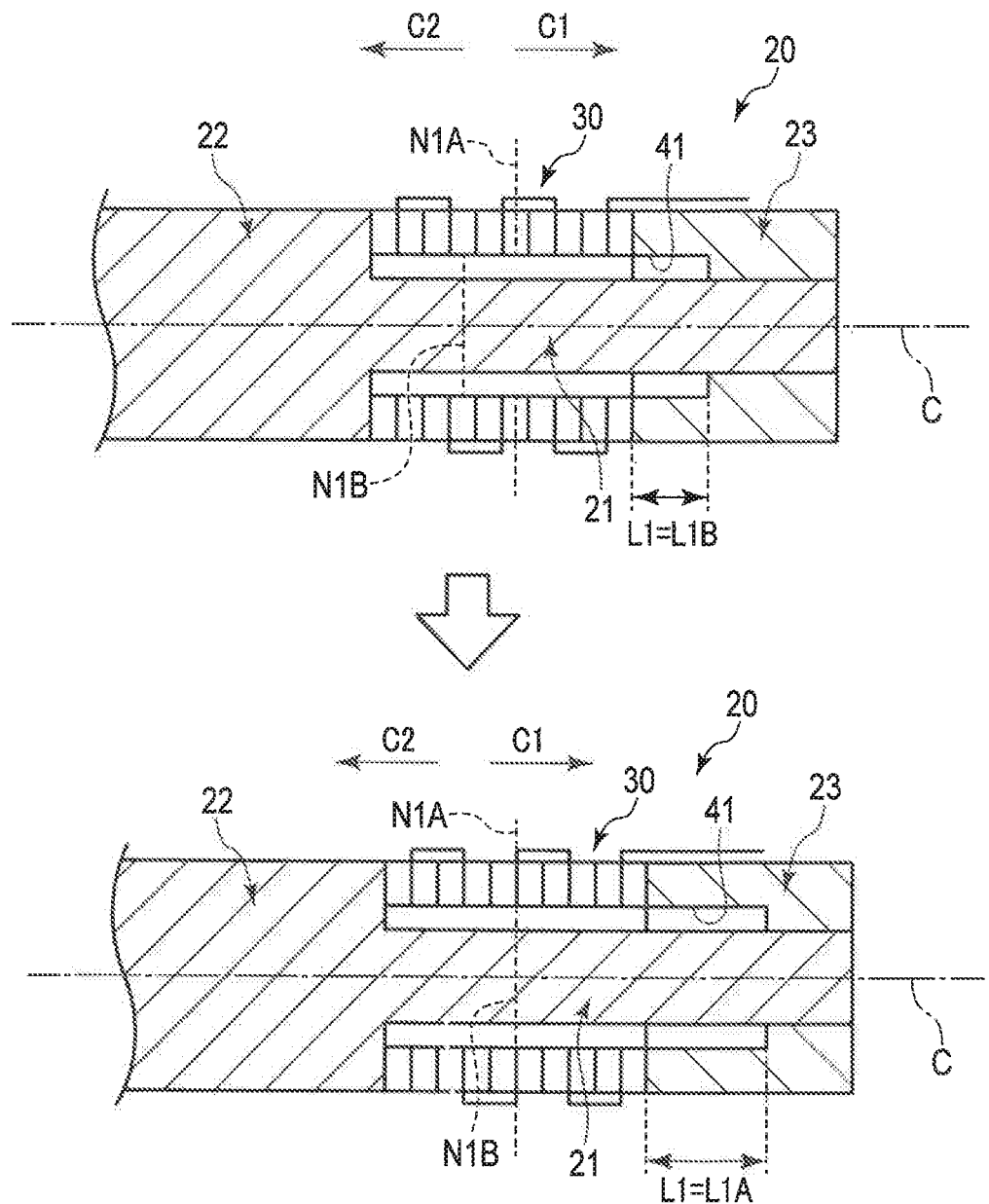
FIG. 5 is a schematic view illustrating an example of a method in which a mutual displacement of a first vibration node and a second vibration node is prevented by adjusting a dimension in a direction along a longitudinal axis of a non-contact portion in a first modification.

In a first modification whose example is illustrated in FIG. 5, the relative position between the vibration nodes N1A and N1B is adjusted by adjusting the dimension L1 in the direction along the longitudinal axis C of the non-contact portion 41. As the dimension L1 changes, the shape and rigidity (mass) of the proximal side block 23 changes. Here, by the proximal side block 23 changing in shape, the vibration state in each of the outer vibration system and the inner vibration system changes. Therefore, the dimension L1 affects each of vibration in the outer vibration system and vibration in the inner vibration system, so that the vibration state is adjusted in each of the outer vibration system and the inner vibration system by adjusting the dimension L1. At this time, the dimension L1 is adjusted so as to adjust the shape of the proximal side block 23 in a manner such that the first vibration node N1A generated in the driving unit 30 (outer vibration system) and the second vibration node N1B generated in the bolt 21 (inner vibration system) are prevented from being displaced with respect to each other in the direction along the longitudinal axis C. Therefore, in this modification, the vibration nodes N1A and N1B are prevented from being displaced with respect to each other due to shape of the proximal side block 23 including the dimension L1.

In the example shown in FIG. 5, in the ultrasonic transducer 20 before the dimension L1 is adjusted, the dimension L1 in the direction along the longitudinal axis C of the non-contact portion 41 corresponds to the dimension L1B. In addition, the second vibration node N1B is positioned on the distal side with respect to the first vibration node N1A. In the example shown in FIG. 5, the dimension L1 is increased from the dimension L1B to the dimension L1A on the basis of the detection result of the relative position between the vibration nodes N1A and N1B. This changes the shape of the proximal side block 23, thereby changing the rigidity, the mass, etc., of the proximal side block 23. In the example shown in FIG. 5, the dimension L1 is increased without changing a material property such as a rigidity modulus of the proximal side block 23. Therefore, by the adjustment of the dimension L1, the rigidity of the proximal side block 23 reduces and the mass of the proximal side block 23 decreases. By the proximal side block 23 changing in shape, the vibration state in each of the outer vibration system and the inner vibration system changes, so that the relative position between the vibration nodes N1A and N1B changes. In the ultrasonic transducer 20 in which the dimension L1 has been adjusted to the dimension L1A the mutual displacement between the vibration nodes N1A and N1B is prevented.

In one modification, the shape of the proximal side block 23 may be adjusted by adjusting both of the distance δ1 in the radial direction from the longitudinal axis C to the non-contact portion 41 and the dimension L1 in the direction along the longitudinal axis C of the non-contact portion 41, so that the vibration state is adjusted in each of the outer vibration system and the inner vibration system this case also, the distance δ1 and the dimension L1 are adjusted so as to adjust the shape of the proximal side block 23 in a manner such that the mutual displacement between the vibration nodes N1A and N1B is prevented.

Figure 6:
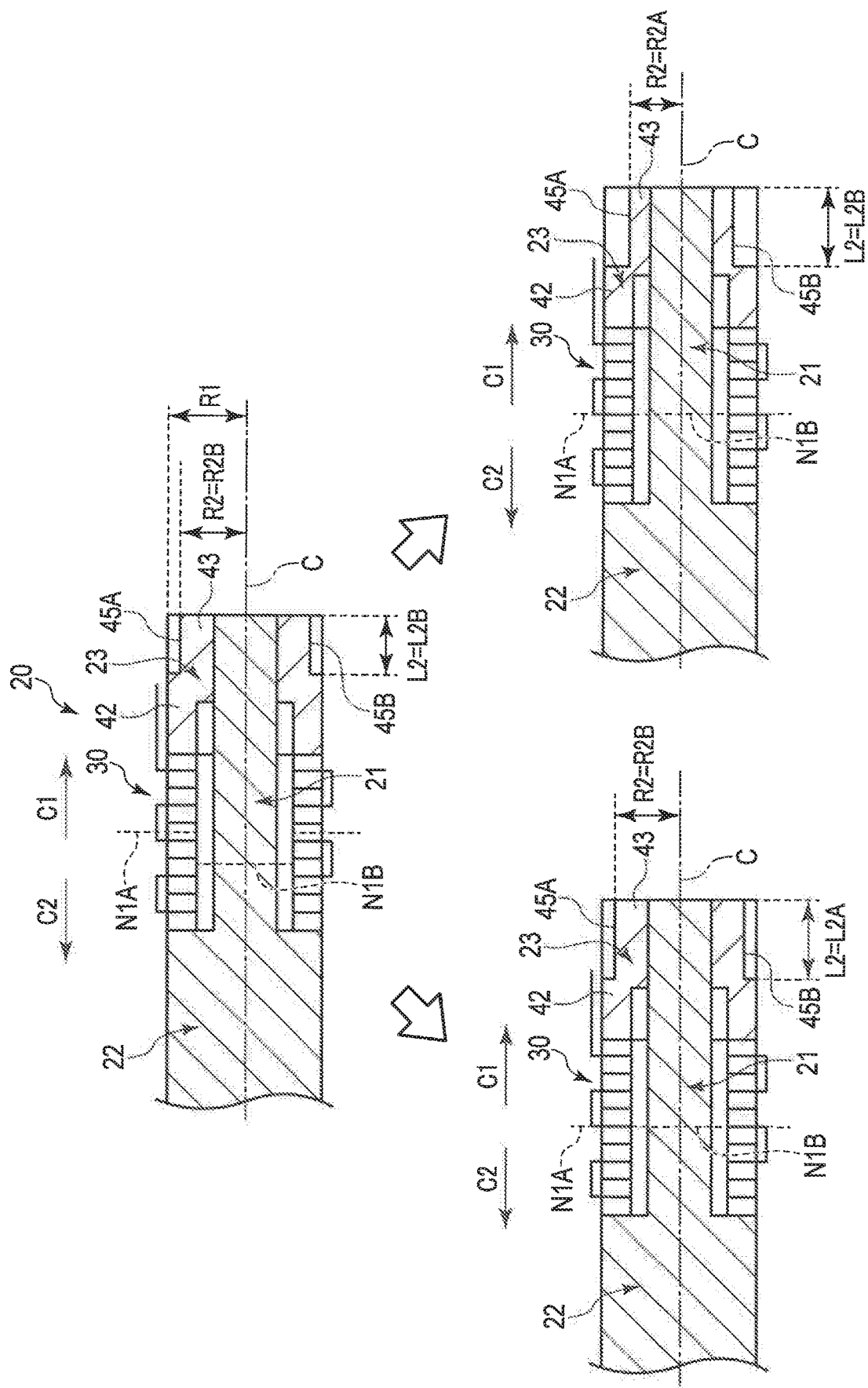
FIG. 6 is a schematic view illustrating an example of a method in which a mutual displacement of a first vibration node and a second vibration node is prevented by adjusting a second area in a second extension region in a second modification, and an example of a method in which a mutual displacement of the first vibration node and the second vibration node is prevented by adjusting a dimension in a direction along a longitudinal axis of a second extension region in a third modification.

In each of the second and third modifications whose examples are illustrated in FIG. 6, the proximal side block 23 as the fastening member has a first extension region 42 and a second extension region 43. The first extension region 42 is extended from the distal end of the proximal side block 23 toward the proximal side. The second extension region 43 is adjacent to the proximal side of the first extension region 42 and is extended up to the proximal end of the proximal side block 23. The outer periphery of the first extension region 42 is formed in a circular shape having a distance R1 from the longitudinal axis C in a cross section substantially perpendicular to the longitudinal axis C. In the first extension region 42, a range surrounded by the outer periphery of the proximal side block 23 in the cross section substantially perpendicular to the longitudinal axis C corresponds to a first area S1. On the other hand, on the outer periphery of the second extension region 43, flat surfaces 45A and 45B are extended from the proximal end to the distal end of the second extension region 43. In this modification, the flat surfaces 45A and 45B are substantially parallel to each other, and each of the flat surfaces 45A and 45B is positioned away from the longitudinal axis C by a distance R2 that is smaller than the distance R1. Furthermore, on the outer periphery of the second extension region 43, each part other than the flat surfaces 45A and 45B forms a circular shape having the distance R1 from the longitudinal axis C in a cross section substantially perpendicular to the longitudinal axis C. In the second extension region 43, therefore, a range surrounded by the outer periphery of the proximal side block 23 in the cross section substantially perpendicular to the longitudinal axis C corresponds to a second area S2 that is smaller than the first area S1.

In the second modification, the second area S2 in the second extension region 43 is adjusted by adjusting the distance R2 from the longitudinal axis C to each of the flat surfaces 45A and 45B, so that the relative position between the vibration nodes N1A and N1B is adjusted. As the distance R2 changes and the second area S2 changes, the shape of the proximal side block 23 changes. As described above, the vibration state in each of the outer vibration system and the inner vibration system changes due to the change in shape of the proximal side block 23. Therefore, the distance R2 and the second area S2 affect the vibration in the outer vibration system and the vibration in the inner vibration system, so that the vibration state is adjusted in each of the outer vibration system and the inner vibration system by adjusting the second area S2. At this time, the distance R2 and the second area S2 are adjusted so as to adjust the shape of the proximal side block 23 in a manner such that the vibration nodes N1A and N1B are prevented from being displaced with respect to each other in the direction along their longitudinal axis C. Therefore, in this modification, the vibration nodes N1A and N1B are prevented from being shifted with respect to each other due to the shape of the proximal side block 23 including the second area S2.

In the example shown in FIG. 6, in the ultrasonic transducer 20 before the distance R2 and the second area S2 are adjusted, the distance R2 from the longitudinal axis C to each of the flat surfaces 45A and 45B corresponds to a distance R2B. In addition, the second vibration node N1B is positioned on the distal side with respect to the first vibration node N1A. In the example shown in FIG. 6, the second area S2 is decreased by decreasing the distance R2 from the distance R2B to the distance R2A on the basis of the detection result of the relative position between the vibration nodes N1A and N1B. This changes the shape of the proximal side block 23, thereby changing the rigidity, the mass, etc., of the proximal side block 23. Here, in the example shown in FIG. 6, the distance R2 and the second area S2 are decreased without changing any material property such as a rigidity modulus of the proximal side block 23. Therefore, by the adjustment of the distance R2 and the second area S2, the rigidity of the proximal side block 23 reduces and the mass of the proximal side block 23 decreases. By the proximal side block 23 changing in shape, the vibration state in each of the outer vibration system and the inner vibration system changes, so that the relative position between the vibration nodes N1A and N1B changes. In the ultrasonic transducer 20 in which the distance R2 has been adjusted to the distance R2A, the mutual displacement of the vibration nodes N1A and N1B is prevented.

In one modification, the outer periphery of the second extension region 43 is formed in a circular shape having the distance R2 smaller than the distance R1 from the longitudinal axis C in a cross section substantially perpendicular to the longitudinal axis C. In this case also, in the second extension region 43, the range surrounded by the outer periphery of the proximal side block 23 in the cross section substantially perpendicular the longitudinal axis C corresponds to the second area S2 that is smaller than the first area S1. In this modification also, the second area S2 in the second extension region 43 is adjusted by adjusting the distance R2, so that the relative position between the vibration nodes N1A and N1B is adjusted, as in the second modification.

In the third modification, the relative position between the vibration nodes N1A and N1B is adjusted by adjusting the dimension L2 in the direction along the longitudinal axis C of the second extension region 43. As the dimension L2 changes, the shape of the proximal side block 23 changes. As described above, the vibration state in each of the outer vibration system and the inner vibration system changes due to the change in shape of the proximal side block 23. Therefore, the dimension L2 affects each of vibration in the outer vibration system and vibration in the inner vibration system, so that the vibration state is adjusted in each of the outer vibration system and the inner vibration system by adjusting the dimension L2. At this time, the dimension L2 is adjusted so as to adjust the shape of the proximal side block 23 in a manner such that the vibration nodes N1A and N1B are prevented from being displaced with respect to each other in the direction along their longitudinal axis C. Therefore, in this modification, the vibration nodes N1A and N1B are prevented from being shifted with respect to each other due to the shape of the proximal side block 23 including the dimension L2.

In the example shown in FIG. 6, in the ultrasonic transducer 20 before the dimension L2 is adjusted, the dimension L2 in the direction along the longitudinal axis C of the second extension region 43 corresponds to the dimension L2B. In addition, the second vibration node N1B is positioned on the distal side with respect to the first vibration node N1A. In the example shown in FIG. 6, the dimension L2 increased from the dimension L2B to the dimension L2A on the basis of the detection result of the relative position between the vibration nodes N1A and N1B. This changes the shape of the proximal side block 23, thereby changing the rigidity, the mass, etc., of the proximal side block 23. Here, in the example shown in FIG. 6, the dimension L2 is increased without changing any material property such as a rigidity modulus of the proximal side block 23. Therefore, by the adjustment of the dimension L2, the rigidity of the proximal side block 23 reduces and the mass of the proximal side block 23 decreases. By the proximal side block 23 changing in shape, the vibration state in each of the outer vibration system and the inner vibration system changes, so that the relative position between the vibration nodes N1A and N1B changes. In the ultrasonic transducer 20 in which the dimension L2 has been adjusted to the dimension L2A, the mutual displacement between the vibration nodes N1A and N1B is prevented.

In one modification, the shape of the proximal side block 23 may be adjusted by adjusting both of the second area S2 in the second extension region and the dimension L2 in the direction along the longitudinal axis C of the second extension region 43 manner such that the vibration state is adjusted in each of the outer vibration system and the inner vibration system. In this case also, the second area S2 and the dimension L2 are adjusted so as to adjust the shape of the proximal side block 23 in a manner such that the mutual displacement between the vibration nodes N1A and N1B is prevented.

Figure 7:
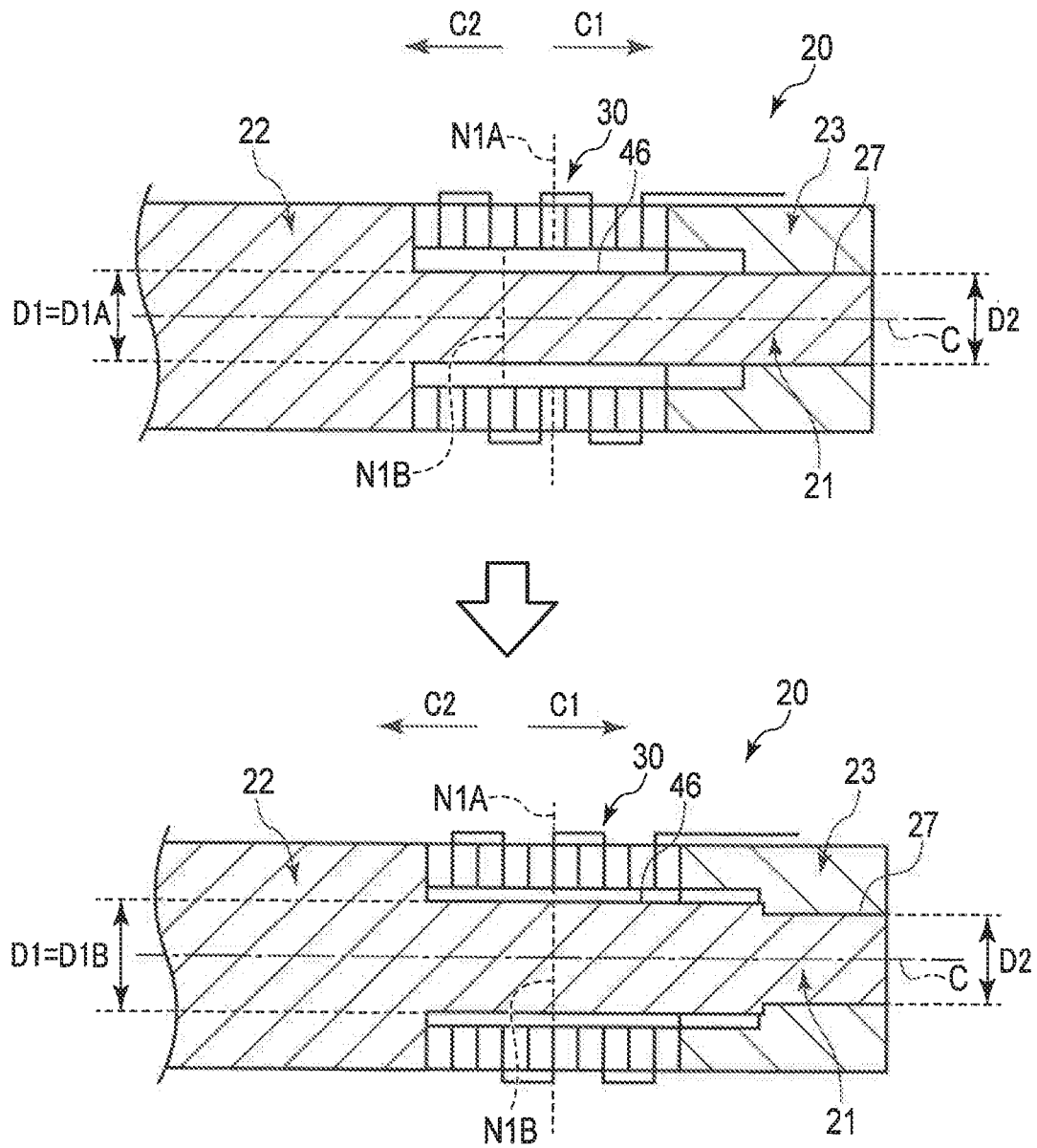
FIG. 7 is a schematic view illustrating an example of a method in which a mutual displacement of a first vibration node and a second vibration node is prevented by adjusting an outer diameter of a bolt in a fourth modification.
Figure 8:
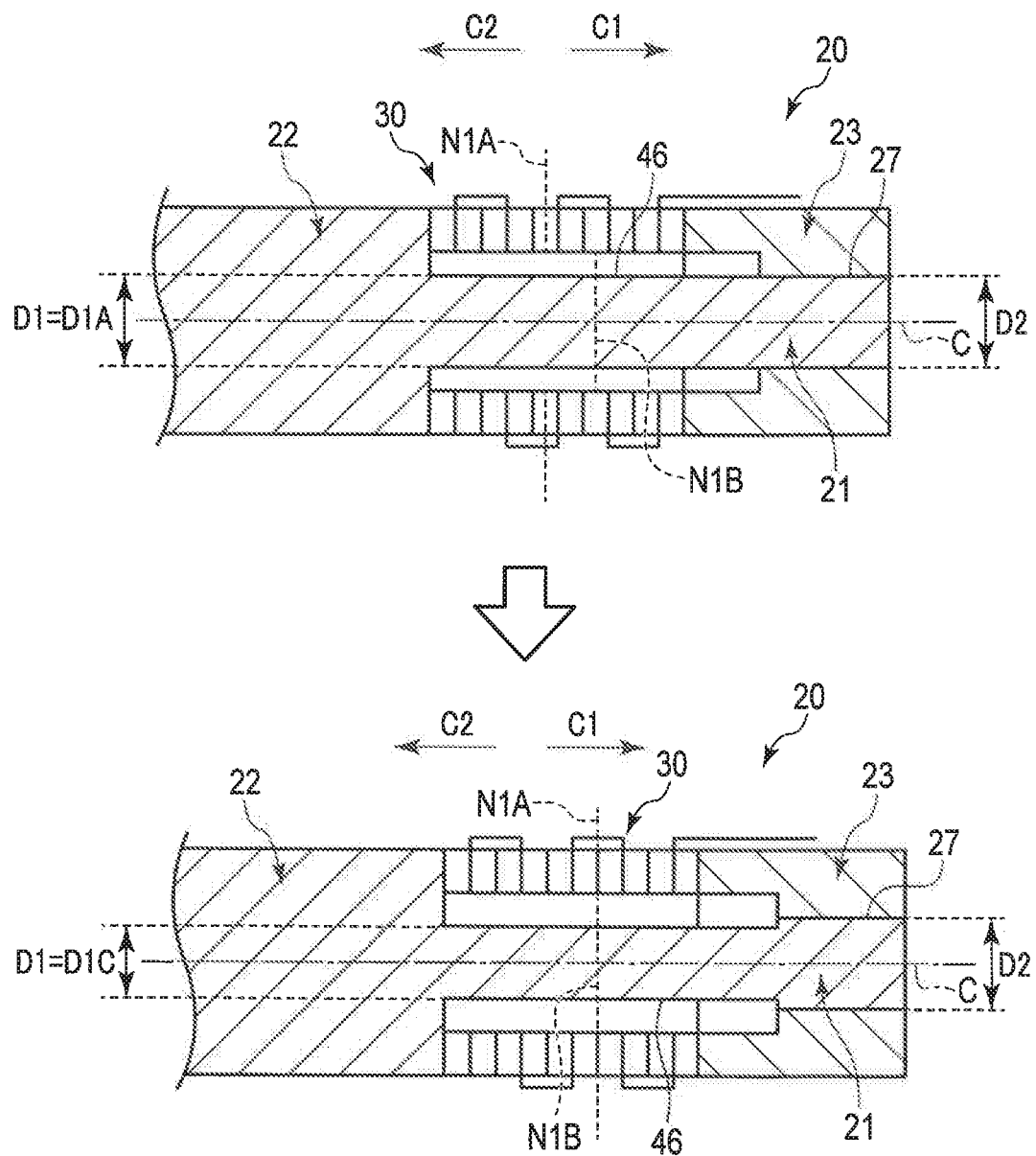
FIG. 8 is a schematic view illustrating another example, which is different from the one shown in FIG. 7, of a method in which the mutual displacement of the first vibration node and the second vibration node is prevented by adjusting the outer diameter of the bolt in the fourth modification.

In the fourth modification whose example is illustrated in FIGS. 7 and 8, the outer periphery of the bolt 21 includes a non-contact outer peripheral portion (bolt body outer periphery portion) 46 in addition to the male screw portion 27. The non-contact outer peripheral portion 46 is extended from a position in which the bolt 21 is connected to the distal side block 22 toward the proximal side. Furthermore, the non-contact outer peripheral portion 46 is adjacent to the distal side of the male screw portion 27. The non-contact outer peripheral portion 46 does not come into contact with the inner periphery of the proximal side block 23 and the inner periphery of the driving unit 30. There is a space between the non-contact outer peripheral portion 46 and the inner periphery of the proximal side block 23 and between the non-contact outer peripheral portion 46 and the inner periphery of the driving unit 30.

In the present modification, the relative position between the vibration nodes N1A and N1B is adjusted by adjusting the outer diameter of the bolt 21 at the non-contact outer peripheral portion 46. Here, the vibration state in each of the outer vibration system and the inner vibration system changes by the rigidity (mass) of the bolt 21 changing due to the change in shape of the bolt 21. Therefore, the outer diameter of the bolt 21 affects each of vibration in the outer vibration system and vibration in the inner vibration system, so that the vibration state in each of the outer vibration system and the inner vibration system is adjusted by adjusting the outer diameter of the bolt 21.

Also, as described above, when the vibration state in each of the outer vibration system and the inner vibration system changes, the relative position between the vibration nodes N1A and N1B changes. Therefore, the bolt 21 is adjusted in shape and rigidity by adjusting its outer diameter, so that the relative position between the vibration nodes N1A and N1B is adjusted. In this modification also, the outer diameter of the bolt 21 is adjusted so as to adjust its shape in a manner such that the first vibration node N1A generated in the driving unit 30 (outer vibration system) and the second vibration node N1B generated in the bolt 21 (inner vibration system) are prevented from being displaced with respect to each other in the direction along the longitudinal axis C. Accordingly, the vibration state in each of the outer vibration system and the inner vibration system is adjusted in a manner such that the mutual displacement between the vibration nodes N1A and N1B is prevented. Therefore, in this modification, the vibration nodes N1A and N1B are prevented from being shifted with respect to each other due to the shape of the bolt 21 including its outer diameter.

In the example shown in FIG. 7, in the ultrasonic transducer 20 before the outer diameter of the bolt 21 is adjusted, the outer diameter D1 of the bolt 21 at the non-contact outer peripheral portion 46 corresponds to an outer diameter D1A. The outer diameter D1A is substantially equal to an outer diameter D2 of the bolt 21 at the male screw portion 27. In addition, the second vibration node N1B is positioned on the distal side with respect to the first vibration node N1A. In the example shown in FIG. 7, the dimension D1 is increased from the dimension D1A to the dimension D1B on the basis of the detection result of the relative position between the vibration nodes N1A and N1B. This changes the shape of the bolt 21, thereby changing the rigidity, the mass, etc., of the bolt 21. Here, in the example shown in FIG. 7, the dimension D1 is increased without changing any material property such as a rigidity modulus of the bolt 21. Therefore, by the adjustment of the diameter D1, the rigidity of the bolt 21 rises and the mass of the bolt 21 increases. By the bolt 21 changing in shape, the vibration state in each of the outer vibration system and the inner vibration system changes, so that the relative position between the vibration nodes N1A and N1B changes. In the ultrasonic transducer 20 in which the outer diameter of the bolt 21 has been adjusted, the mutual displacement between the vibration nodes N1A and N1B is prevented.

In the example shown in FIG. 8 also, in the ultrasonic transducer 20 before the outer diameter of the bolt 21 is adjusted, the outer diameter D1 of the bolt 21 at the non-contact outer peripheral portion 46 corresponds to an outer diameter D1A, as in the example shown in FIG. 7. However, in the example shown in FIG. 8, unlike the example in FIG. 7, the second vibration node N1B is positioned on the proximal side with respect to the first vibration node N1A. In the example shown in FIG. 8, the outer diameter D1 is decreased from the outer diameter D1A to the outer diameter D1C on the basis of the detection result of the relative position between the vibration nodes N1A and N1B. This changes the shape of the bolt 21, thereby changing the rigidity, the mass, etc., of the bolt 21. Here, in the example shown in FIG. 8, the outer diameter D1 is decreased without changing any material property such as a rigidity modulus of the bolt 21. Therefore, by the adjustment of the outer diameter D1, the rigidity of the bolt 21 reduces and the mass of the bolt 21 decreases. By the bolt 21 changing in shape, the vibration state in each of the outer vibration system and the inner vibration system changes, so that the relative position between the vibration nodes N1A and N1B changes. Then, in the ultrasonic transducer 20 in which the outer diameter of the bolt 21 has been adjusted, the mutual displacement between the vibration nodes N1A and N1B is prevented.

Figure 9:
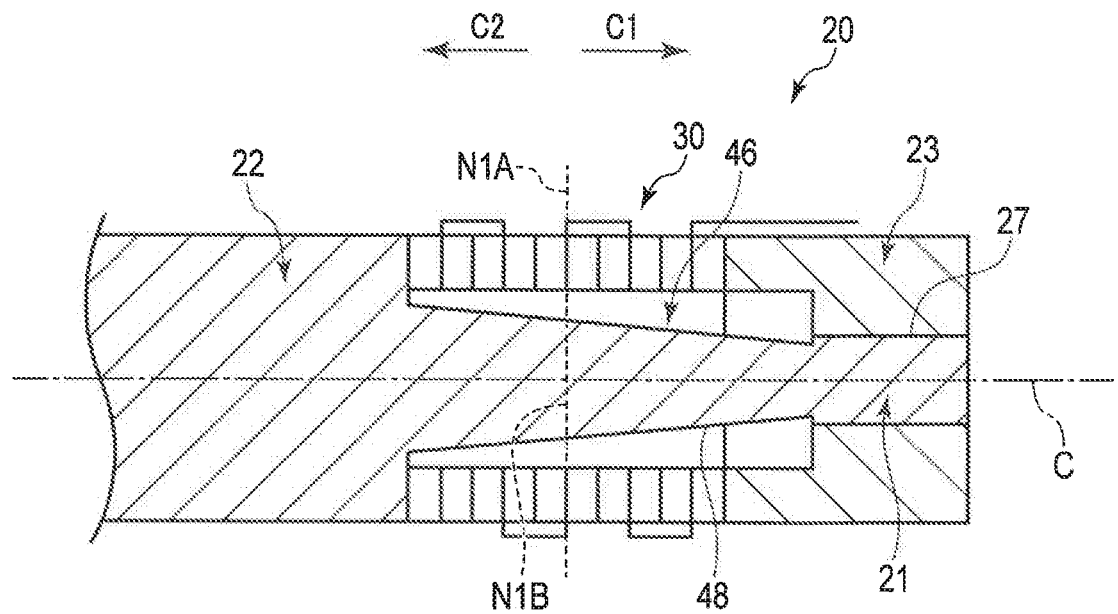
FIG. 9 is a cross-sectional view schematically illustrating a configuration of an ultrasonic transducer according to a fifth modification.

Furthermore, in the fifth modification shown in FIG. 9, the non-contact outer peripheral portion 46 of the bolt 21 is provided with a tapered portion 48 whose outer diameter gradually decreases toward the proximal side. In this modification, the bolt 21 is adjusted in shape, rigidity, etc., by the tapered portion 48 so that the mutual displacement of the vibration nodes N1A and N1B is prevented. Therefore, in this modification also, the outer diameter of the bolt 21 is adjusted so as to adjust its shape in a manner such that the mutual displacement between the vibration nodes N1A and N1B is prevented. In one modification, the shape of the bolt 21 may be adjusted by providing the non-contact outer peripheral portion 46 with a tapered portion (not shown) whose outer diameter gradually increases toward the proximal side in a manner such that this tapered portion prevents the mutual displacement between the vibration nodes N1A and N1B.

Figure 10:
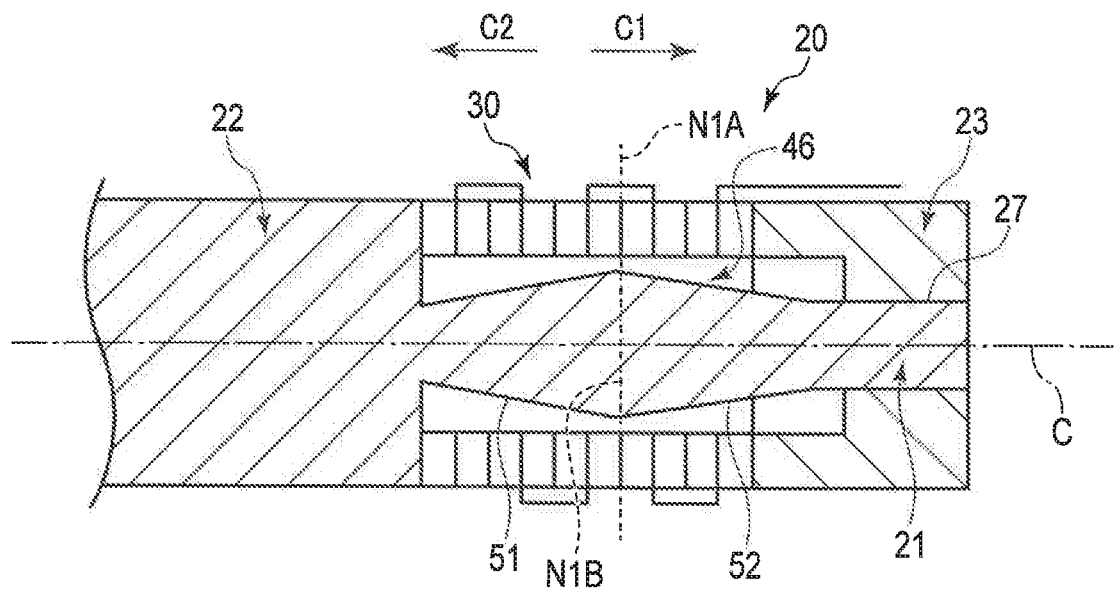
FIG. 10 is a cross-sectional view schematically illustrating a configuration of an ultrasonic transducer according to a sixth modification.

Furthermore, in the sixth modification shown in FIG. 10, the non-contact outer peripheral portion 46 of the bolt 21 is provided with tapered portions 51 and 52. In the tapered portion 51, its outer diameter gradually increases toward the proximal side. In the tapered portion 52, its outer diameter gradually decreases toward the proximal side. Furthermore, the tapered portion 52 is continuous with the proximal side of the tapered portion 51. In this modification, the outer diameter of the bolt 21 is adjusted so as to adjust its shape in a manner such that the second vibration node N1B is positioned in the boundary between the tapered portions 51 and 52. The mutual displacement between the vibration nodes N1A and N1B is prevented by adjusting the shape of the bolt 21 in a manner such that the second vibration node N1B is positioned the boundary between the tapered portions 51 and 52. Therefore, in this modification also, the outer diameter of the bolt 21 is adjusted so as to adjust its shape in a manner such that the mutual displacement between the vibration nodes N1A and N1B is prevented.

Figure 11:
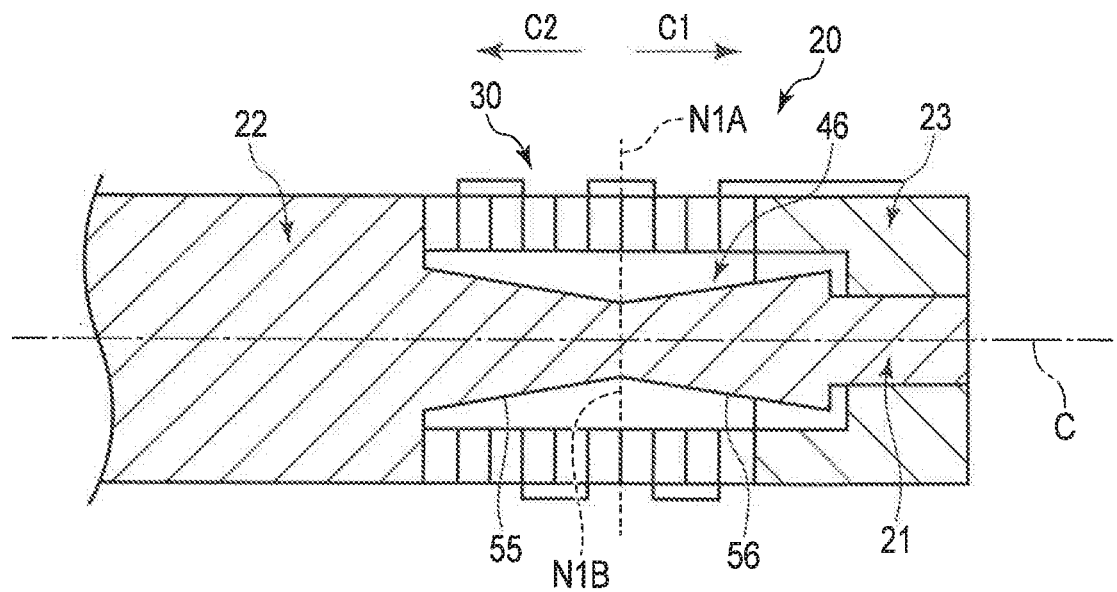
FIG. 11 is a cross-sectional view schematically illustrating a configuration of an ultrasonic transducer according to a seventh modification.

Furthermore, in the seventh modification shown in FIG. 11, the non-contact outer peripheral portion 46 is provided with the tapered portions 55 and 56. In the tapered portion 55, its outer diameter gradually decreases toward the proximal side. In the tapered portion 56, its outer diameter gradually increases toward the proximal side. Furthermore, the tapered portion 56 is continuous with the proximal side of the tapered portion 55. In this modification, the outer diameter of the bolt 21 is adjusted so as to adjust its shape in a manner such that the second vibration node N1B is positioned in the boundary between the tapered portions 55 and 56. The mutual displacement between the vibration nodes N1A and N1B is prevented by adjusting the shape of the bolt 21 in a manner such that the second vibration node N1B is positioned in the boundary between the tapered portions 55 and 56. Therefore, in this modification also, the outer diameter of the bolt 21 is adjusted so as to adjust its shape in a manner such that the mutual displacement between the vibration nodes N1A and N1B is prevented.

In one modification, the bolt 21 may be adjusted in rigidity, mass, etc., by adjusting its shape by adjusting the outer diameter of the bolt 21 at the male screw portion 27. In another modification, the bolt 21 may be adjusted in rigidity, mass, etc., by adjusting its shape by adjusting a screw pitch at the male screw portion 27. In each of those modifications also, the shape of the bolt 21 is adjusted in a manner such that the mutual displacement between the vibration nodes N1A and N1B is prevented.

In one modification, the relative position between the vibration nodes N1A and N1B is adjusted by adjusting a material property of at least one of the distal side block 22 and the proximal side block 23. Here, the vibration state in each of the outer vibration system and the inner vibration system changes as either of the distal side block 22 and the proximal side block 23 changes in material property such as a rigidity modulus, a density, etc., and either of the distal side block 22 and the proximal side block 23 changes in rigidity (mass). Therefore, a material property of each of the distal side block 22 and the proximal side block 23 affects each of vibration in the outer vibration system and vibration in the inner vibration system, so that the vibration state in each of the outer vibration system and the inner vibration system is adjusted by adjusting a material property of either of the distal side block 22 and the proximal side block 23.

Also, as described above, when the vibration state in each of the outer vibration system and the inner vibration system changes, the relative position between the vibration nodes N1A and N1B changes. Therefore, either of the distal side block 22 and the proximal side block 23 is adjusted in rigidity and mass, etc., by adjusting a material property of either of the distal side block 22 and the proximal side block 23. By this adjustment, the relative position between the vibration nodes N1A and N1B is adjusted. In this modification also, a material property of either of the distal side block 22 and the proximal side block 23 is adjusted in a manner such that the first vibration node N1A generated in the driving unit 30 and the second vibration node N1B generated in the bolt 21 are prevented from being displaced with respect to each other in the direction along the longitudinal axis C. Accordingly, the vibration state in each of the outer vibration system and the inner vibration system is adjusted in a manner such that the mutual displacement between the vibration nodes N1A and N1B is prevented. Therefore, in this modification, the vibration nodes N1A and N1B are prevented from being shifted with respect to each other due to at least one of a material property of the distal side block 22 and a material property of the proximal side block 23.

In one example, in the ultrasonic transducer 20 before adjusted, the second vibration node N1B is positioned on the distal side with respect to the first vibration node N1A. In this case, the rigidity modulus of the proximal side block 23 is decreased by adjusting a material property of the proximal side block 23 on the basis of the detection result of the relative position between the vibration nodes N1A and N1B. In this case, the rigidity modulus of the proximal side block 23 is decreased without changing the shape of the proximal side block 23. Therefore, by the adjustment of a material property, the rigidity of the proximal side block 23 is decreased and the mass of the proximal side block 23 is reduced. Instead of adjusting a material property of the proximal side block 23, a material property of the distal side block 22 may be adjusted to increase the rigidity modulus of the distal side block 22. In this case, the rigidity modulus of the distal side block 22 is increased without changing the shape of the distal side block 22. Therefore, by the adjustment of a material property, the rigidity of the distal side block 22 rises and the mass of the distal side block 22 increases. As described above, by the distal side block 22 or the proximal side block 23 changing in material property, the vibration state changes in each of the outer vibration system and the inner vibration system, and the relative position of the vibration nodes N1A, N1B changes. In the ultrasonic transducer 20 in which the proximal side block 23 or the distal side block 22 has been adjusted in material property, the mutual displacement between the vibration nodes N1A and N1B is prevented.

Furthermore, the relative position between the vibration nodes N1A and N1B may be adjusted by combining some of the embodiments, etc., described above. For example, in one modification, the relative position between the vibration nodes N1A and N1B is adjusted by adjusting both the shape of the proximal side block 23 and the shape of the bolt 21. In another modification, the relative position between the vibration nodes N1A and N1B is adjusted by adjusting the shape of the proximal side block 23 and the material property of the proximal side block 23.

Figure 12:
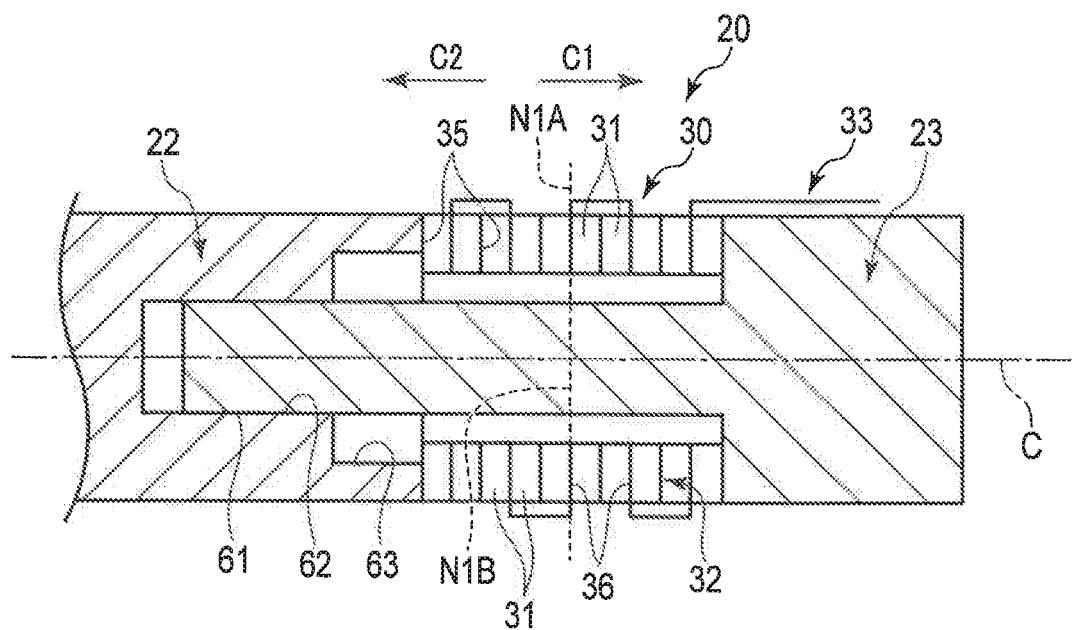
FIG. 12 is a cross-sectional view schematically illustrating a configuration of an ultrasonic transducer according to an eighth modification.

Furthermore, in the eighth modification shown in FIG. 12, the bolt 21 is formed integrally with the proximal side block 23. In this case, the distal portion of the outer periphery of the bolt 21 is provided with a male screw portion 61 as a first engagement. The proximal portion of the distal side block 22 is provided a female screw portion 62 as a second engagement that is engageable with the first engagement. In this modification, by engaging the female screw portion 62 with the male screw portion 61, that is, by screwing them together, the distal side block 22 is fastened to the outer periphery of the bolt 21. Therefore, in this modification, the distal side block 22 is a fastening member that is fastened to the outer periphery of the bolt 21. In this modification, the distal side block 22 is provided with a non-contact portion 63 spaced apart from the outer periphery of the bolt 21. The non-contact portion 63 is extended from the proximal end of the distal side block 22 toward the distal side so that the non-contact portion 63 is adjacent to the proximal side of the female screw portion 62 as the second engagement. In this modification, a concave shape is formed. This concave shape is concaved from the proximal end of the distal side block 22 toward the distal side and is composed of the female screw portion 62 and the non-contact portion 63.

In this modification also, in the state in which the ultrasonic transducer 20 is vibrating by ultrasonic vibration generated in the piezoelectric elements 31, the first vibration node N1A is generated in the driving unit 30, while the second vibration node N1B is generated in the bolt 21. In this modification, the outer vibration system is composed of the driving unit 30 and a part of the distal side block 22, while the inner vibration system is composed of the bolt 21.

In the modification, for example, the shape and the rigidity of the distal side block 22 are adjusted by adjusting a distance from the longitudinal axis C to the non-contact portion 63, thereby adjusting the vibration state in each of the outer vibration system and the inner vibration system. In this modification also, the vibration state in each of the outer vibration system and the inner vibration system is adjusted in a manner such that the mutual displacement between the ration nodes N1A and N1B is prevented. In this modification also, instead of adjusting the shape of the distal side block 22, or in addition to adjusting the shape of the distal side block 22, the shape of the bolt 21 may be adjusted. By the bolt 21 being adjusted in shape, the vibration state in each of the outer vibration system and the inner vibration system is adjusted, so that the relative position between the vibration nodes N1A and N1B is adjusted. In this modification also, instead of adjusting the shape of the distal side block 22, or in addition to adjusting the shape of the distal side block 22, a material property of either of the distal side block 22 and the proximal side block 23 may be adjusted. The vibration state in each of the outer vibration system and the inner vibration system is adjusted by adjusting a material property of either of the distal side block and the proximal side block 23, so that the relative position between the vibration nodes N1A and N1B is adjusted.

In the embodiments, etc., described above, the ultrasonic transducer (20) includes the bolt (21) extended along the longitudinal axis (C) from the proximal end to the distal end, the distal side block (22) to which one distal portion of the bolt (21) is connected, and the proximal side block (23) to which the proximal portion of the bolt (21) is connected. The ultrasonic transducer (20) includes the driving unit (30) that is attached to the outer periphery of the bolt (21) in a state in which the driving unit (30) is sandwiched between the distal side block (22) and the proximal side block (23) in the direction along the longitudinal axis (C). The driving unit (30) includes the piezoelectric elements (31) that generate ultrasonic vibration by an electric energy being supplied. By transmission of ultrasonic vibration generated in the piezoelectric element (31), the ultrasonic transducer (20) vibrates in a state in which the first vibration node (N1A) generated in the driving unit (30) and the second vibration node (N1B) generated in the bolt (21) are prevented from being displaced with each other in the direction along the longitudinal axis (C).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic transducer comprising:
   a bolt extending along a longitudinal axis from a proximal end to a distal end;
   a distal side block to which a distal portion of the bolt is connected;
   a proximal side block to which a proximal portion of the bolt is connected; and
   a driving source attached to an outer periphery of the bolt, and sandwiched between the distal side block and the proximal side block in a direction along the longitudinal axis,
   the driving source including a piezoelectric element configured to generate ultrasonic vibration from an electric energy supplied thereto, and
   the driving source being configured to vibrate together with the bolt, the distal side block, and the proximal side block in a state in which a first vibration node that is generated in the driving source and a second vibration node that is generated in the bolt are prevented from being displaced with respect to each other in the direction along the longitudinal axis.

2. The ultrasonic transducer according to claim 1, wherein:
   a shape of the distal side block and a shape of the proximal side block affect vibration in the driving source in which the first vibration node is generated and vibration in the bolt in which the second vibration node is generated; and
   in a state in which the ultrasonic transducer vibrates, the first vibration node and the second vibration node are prevented from being displaced with respect to each other in the direction along with the longitudinal axis due to at least one of the shape of the distal side block and the shape of the proximal side block.

3. The ultrasonic transducer according to claim 2, wherein:
   the bolt includes a first fastener provided on the outer periphery of the bolt;
   one of the distal side block and the proximal side block includes a second fastener engaged with the first fastener, and serves as a connector which is fastened to the outer periphery of the bolt by engagement of the second fastener with the first fastener;
   a shape of the connector affects the vibration in the driving source and the vibration in the bolt; and
   in a state in which the ultrasonic transducer vibrates, the first vibration node and the second vibration node are prevented from being displaced with respect to each other in the direction along the longitudinal axis due to the shape of the connector.

4. The ultrasonic transducer according to claim 3, wherein:
   an inner surface of the connector includes a non-contact portion that is spaced apart from the outer periphery of the bolt and is disposed at a position different from the second fastener;
   a distance in a radial direction from the longitudinal axis to the non-contact portion and a dimension in the direction along the longitudinal axis of the non-contact portion affect the vibration in the driving source and the vibration in the bolt; and
   in a state in which the ultrasonic transducer vibrates, the first vibration node and the second vibration node are prevented from being displaced with respect to each other in the direction along the longitudinal axis due to at least one of the distance to the non-contact portion and the dimension of the non-contact portion.

5. The ultrasonic transducer according to claim 3, wherein:
the connector includes:
a first extension region having a first cross-sectional area perpendicular to the longitudinal axis, and
a second extension region which is adjacent to the first extension region in the direction along the longitudinal axis, and has a second cross-sectional area perpendicular to the longitudinal axis that is smaller than the first cross-sectional area;
the second cross-sectional area in the second extension region and a dimension in the direction along the longitudinal axis of the second extension region affect the vibration in the driving source and the vibration in the bolt; and
in a state in which the ultrasonic transducer vibrates, the first vibration node and the second vibration node are prevented from being displaced with respect to each other in the direction along the longitudinal axis due to at least one of the second cross-sectional area in the second extension region and the dimension of the second extension region.

6. The ultrasonic transducer according to claim 1, wherein:
a shape of the bolt affects vibration in the driving source in which the first vibration node is generated and vibration in the bolt in which the second vibration node is generated; and
in a state in which the ultrasonic transducer vibrates, the first vibration node and the second vibration node are prevented from being displaced with respect to each other in the direction along the longitudinal axis due to the shape of the bolt.

7. The ultrasonic transducer according to claim 6, wherein:
an outer diameter of the bolt affects the vibration in the driving source and the vibration in the bolt; and
in a state in which the ultrasonic transducer vibrates, the first vibration node and the second vibration node are prevented from being displaced with respect to each other in the direction along the longitudinal axis due to the outer diameter of the bolt.

8. The ultrasonic transducer according to claim 1, wherein:
a material property of the distal side block and a material property of the proximal side block affect vibration in the driving source in which the first vibration node is generated and vibration in the bolt in which the second vibration node is generated; and
in a state in which the ultrasonic transducer vibrates, the first vibration node and the second vibration node are prevented from being displaced with respect to each other in the direction along the longitudinal axis due to at least one of the material property of the distal side block and the material property of the proximal side block.

9. The ultrasonic transducer according to claim 1, wherein:
the bolt includes a first fastener provided on the outer periphery of the bolt;
one of the distal side block and the proximal side block includes a second fastener engaged with the first fastener, and serves as a connector that is fastened to the outer periphery of the bolt by engagement of the second fastener with the first fastener; and an inner surface of the connector includes a non-contact portion that is spaced apart from the outer periphery of the bolt, and is disposed at a position different from the second fastener.

10. The ultrasonic transducer according to claim 9, wherein:
a distance in a radial direction from the longitudinal axis to the non-contact portion is larger than a distance in the radial direction from the longitudinal axis to an inner periphery of the driving source.

11. The ultrasonic transducer according to claim 1, wherein:
the bolt includes a first fastener provided on the outer periphery of the bolt;
one of the distal side block and the proximal side block includes a second fastener engaged with the first engagement, and serves as a connector that is fastened to the outer periphery of the bolt by engagement of the second fastener with the first fastener; and
the connector includes:
a first extension region having a first cross-sectional area perpendicular to the longitudinal axis, and
a second extension region which is adjacent to the first extension region in the direction along the longitudinal axis, and has a second cross-sectional area perpendicular to the longitudinal axis that is smaller than the first cross-sectional area.

12. The ultrasonic transducer according to claim 1, wherein:
the bolt includes a first fastener provided on the outer periphery of the bolt;
one of the distal side block and the proximal side block includes a second fastener engaged with the first fastener, and serves as a connector that is fastened to the outer periphery of the bolt by engagement of the second fastener with the first fastener;
an outer periphery of the bolt includes a non-contact outer peripheral portion spaced apart from an inner periphery of the connector and an inner periphery of the driving source, the non-contact outer peripheral portion being disposed at a position different from the first fastener; and
an outer diameter of the bolt at the non-contact outer peripheral portion is different from an outer diameter of the bolt at the first fastener.

13. A method for manufacturing an ultrasonic transducer, the method comprising:
attaching a driving source including a piezoelectric element to an outer periphery of a bolt which extends along a longitudinal axis from a proximal end to a distal end;
sandwiching the driving source between a distal side block, to which a distal portion of the bolt is connected, and a proximal side block, to which a proximal portion of the bolt is connected, in a direction along the longitudinal axis;
vibrating the driving source together with the bolt, the distal side block, and the proximal side block by via ultrasonic vibration generated by the piezoelectric element from an electric energy supplied thereto;
detecting a relative position in the direction along the longitudinal axis between a first vibration node generated in the driving unit and a second vibration node generated in the bolt in a state in which the bolt, the distal side block, the proximal side block, and the driving unit vibrate together; and adjusting, based on the detected relative position between the first vibration node and the second vibration node, a vibration state in the driving source in which the first vibration node is generated and a vibration state in the bolt in which the second vibration node is generated in a manner such that the first vibration node and the second vibration node are prevented from being displaced with respect to each other in the direction along the longitudinal axis.

14. The method according to claim 13, wherein adjusting the vibration state in each of the driving source and the bolt includes at least one of:
adjusting a shape of at least one of the distal side block, the proximal side block, and the bolt; and
adjusting a material property of at least one of the distal side block and the proximal side block.

15. The method according to claim 13, wherein detecting the relative position between the first vibration node and the second vibration node includes:
detecting an output current and an output voltage related to the electric energy to be supplied to the piezoelectric element; and
detecting the relative position between the first vibration node and the second vibration node on a basis of a phase difference between the output current and the output voltage.

16. The method according to claim 15, wherein detecting the relative position between the first vibration node and the second vibration node on a basis of the phase difference between the output current and the output voltage includes determining that the first vibration node and the second vibration node are displaced with respect to each other in the direction along the longitudinal axis based on a determination that: (i) the phase difference is inverted between positive and negative after supply of the electric energy to the piezoelectric element has started, and (ii) after the phase difference is inverted between positive and negative, an absolute value of the phase difference becomes larger than a predetermined threshold without the phase difference being inverted between positive and negative.

17. The ultrasonic transducer according to claim 1, wherein the first vibration node is aligned with the second vibration node.

18. The method according to claim 13, wherein:
the bolt includes a first fastener provided on the outer periphery of the bolt;
one of the distal side block and the proximal side block includes a second fastener engaged with the first fastener, and serves as a connector which is fastened to the outer periphery of the bolt by engagement of the second fastener with the first fastener;
an inner surface of the connector includes a non-contact portion that is spaced apart from the outer periphery of the bolt and is disposed at a position different from the second fastener; and
the vibration state in each of the driving source and the bolt is adjusted by adjusting at least one of a distance in a radial direction from the longitudinal axis to the non-contact portion and a dimension in the direction along the longitudinal axis of the non-contact portion.

19. The method according to claim 13, wherein:
the bolt includes a first fastener provided on the outer periphery of the bolt;
one of the distal side block and the proximal side block includes a second fastener engaged with the first fastener, and serves as a connector which is fastened to the outer periphery of the bolt by engagement of the second fastener with the first fastener;
the connector includes:
a first extension region having a first cross-sectional area perpendicular to the longitudinal axis, and
a second extension region which is adjacent to the first extension region in the direction along the longitudinal axis, and has a second cross-sectional area perpendicular to the longitudinal axis that is smaller than the first cross-sectional area; and
the vibration state in each of the driving source and the bolt is adjusted by adjusting at least one of the second cross-sectional area in the second extension region and a dimension in the direction along the longitudinal axis of the second extension region.

20. The method according to claim 13, wherein:
the bolt includes a first fastener provided on the outer periphery of the bolt;
one of the distal side block and the proximal side block includes a second fastener engaged with the first fastener, and serves as a connector that is fastened to the outer periphery of the bolt by engagement of the second fastener with the first fastener;
an outer periphery of the bolt includes a non-contact outer peripheral portion spaced apart from an inner periphery of the connector and an inner periphery of the driving source, the non-contact outer peripheral portion being disposed at a position different from the first fastener;
the vibration state in each of the driving source and the bolt is adjusted by adjusting at least one of the outer diameter and shape of the bolt at the non-contact outer peripheral portion.

* * * * *